(12) United States Patent
McConnell et al.

(10) Patent No.: US 9,463,311 B2
(45) Date of Patent: *Oct. 11, 2016

(54) VALVES, VALVED FLUID TRANSFER DEVICES AND AMBULATORY INFUSION DEVICES INCLUDING THE SAME

(71) Applicant: Medallion Therapeutics, Inc., Valencia, CA (US)

(72) Inventors: Susan McConnell, Woodland Hills, CA (US); Keith A. Oberg, Valencia, CA (US); Lawrence S. Ring, Valencia, CA (US); Peter C. Lord, Kihei, HI (US)

(73) Assignee: Medallion Therapeutics, Inc., Valencia, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/594,114

(22) Filed: Jan. 10, 2015

(65) Prior Publication Data

US 2015/0238748 A1 Aug. 27, 2015

Related U.S. Application Data

(63) Continuation of application No. 14/049,076, filed on Oct. 8, 2013, now Pat. No. 8,936,580, which is a continuation of application No. 13/594,737, filed on Aug. 24, 2012, now Pat. No. 8,551,055, which is a continuation of application No. 12/054,009, filed on Mar. 24, 2008, now Pat. No. 8,251,960.

(60) Provisional application No. 60/896,910, filed on Mar. 24, 2007.

(51) Int. Cl.
*A61M 39/22* (2006.01)
*A61M 5/142* (2006.01)
*A61M 5/168* (2006.01)
*F16K 1/32* (2006.01)

(52) U.S. Cl.
CPC ......... *A61M 39/22* (2013.01); *A61M 5/14216* (2013.01); *A61M 5/14276* (2013.01); *A61M 5/16804* (2013.01); *A61M 5/16881* (2013.01); *F16K 1/32* (2013.01); *A61M 2039/226* (2013.01); *A61M 2205/0222* (2013.01)

(58) Field of Classification Search
CPC ......... A61M 2039/226; A61M 39/22; A61M 5/16804; F16K 1/32
See application file for complete search history.

(56) References Cited

U.S. PATENT DOCUMENTS

| | | |
|---|---|---|
| 4,838,887 A | 6/1989 | Idriss |
| 4,883,467 A | 11/1989 | Franetzki et al. |
| 5,158,547 A | 10/1992 | Doan et al. |
| 5,281,210 A | 1/1994 | Burke et al. |
| 5,368,274 A | 11/1994 | Falk et al. |
| 5,466,218 A | 11/1995 | Srisathapat et al. |
| 5,725,017 A | 3/1998 | Elsberry et al. |
| 6,152,898 A | 11/2000 | Olsen |
| 6,227,818 B1 | 5/2001 | Falk et al. |
| 6,228,050 B1 | 5/2001 | Olsen et al. |
| 6,250,331 B1 * | 6/2001 | Nardi .................. A61M 1/0005 137/247.11 |

(Continued)

FOREIGN PATENT DOCUMENTS

| | | |
|---|---|---|
| EP | 0 104 787 B1 | 2/1987 |
| WO | WO 2006/074036 A2 | 7/2006 |

*Primary Examiner* — Imani Hayman
(74) *Attorney, Agent, or Firm* — Henricks, Slavin Holmes LLP

(57) ABSTRACT

Valves, valved fluid transfer devices and ambulatory infusion devices including the same.

18 Claims, 15 Drawing Sheets

(56) References Cited

U.S. PATENT DOCUMENTS

| | | |
|---|---|---|
| 6,264,439 B1 | 7/2001 | Falk et al. |
| 6,299,419 B1 | 10/2001 | Hunklinger et al. |
| 6,454,548 B2 | 9/2002 | Falk et al. |
| 6,770,067 B2 | 8/2004 | Lorenzen et al. |
| 6,796,777 B2 | 9/2004 | Falk et al. |
| 6,892,755 B2 | 5/2005 | Black |
| 6,902,544 B2 | 6/2005 | Ludin et al. |
| 7,131,967 B2 | 11/2006 | Gray et al. |
| 7,510,552 B2 | 3/2009 | Lebel et al. |
| 7,785,293 B2 | 8/2010 | Gray et al. |
| 7,867,221 B2 | 1/2011 | Haase |
| 8,251,960 B2 | 8/2012 | McConnell et al. |
| 8,551,055 B2 | 10/2013 | McConnell et al. |
| 8,936,579 B2 | 1/2015 | McConnell et al. |
| 8,936,580 B2 | 1/2015 | McConnell et al. |
| 2002/0081222 A1* | 6/2002 | Karp .................. F04B 43/043 417/507 |
| 2005/0159714 A1 | 7/2005 | Gibson et al. |
| 2006/0224145 A1 | 10/2006 | Gillis et al. |
| 2007/0269322 A1 | 11/2007 | Falk et al. |
| 2008/0234638 A1 | 9/2008 | Antonio et al. |
| 2008/0234639 A1 | 9/2008 | Antonio et al. |
| 2009/0197078 A1 | 8/2009 | Vissing et al. |
| 2013/0296786 A1 | 11/2013 | McConnell et al. |
| 2014/0121599 A1 | 5/2014 | McConnell et al. |
| 2014/0121600 A1 | 5/2014 | McConnell et al. |

* cited by examiner

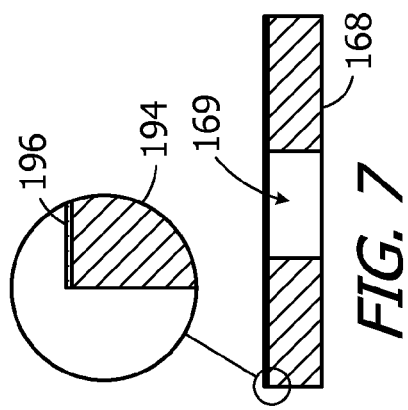
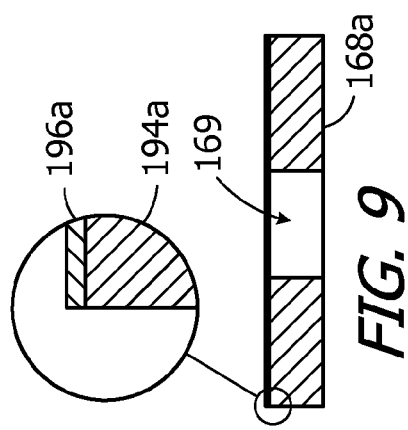
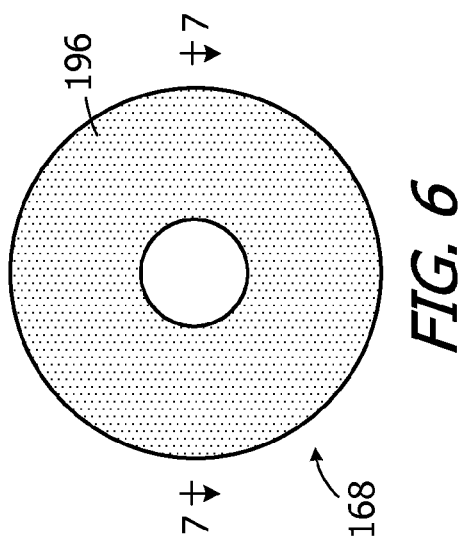
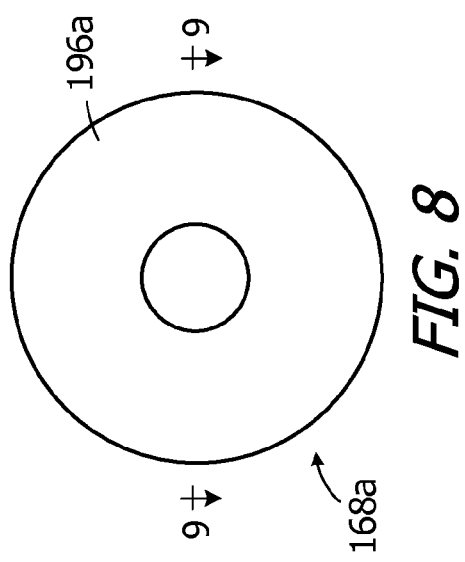

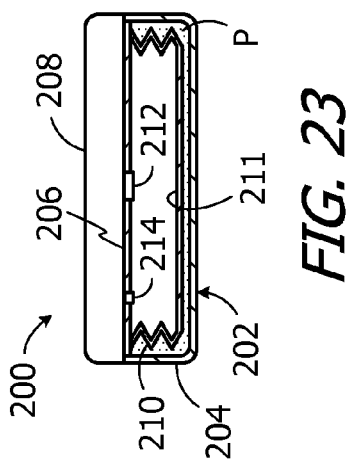
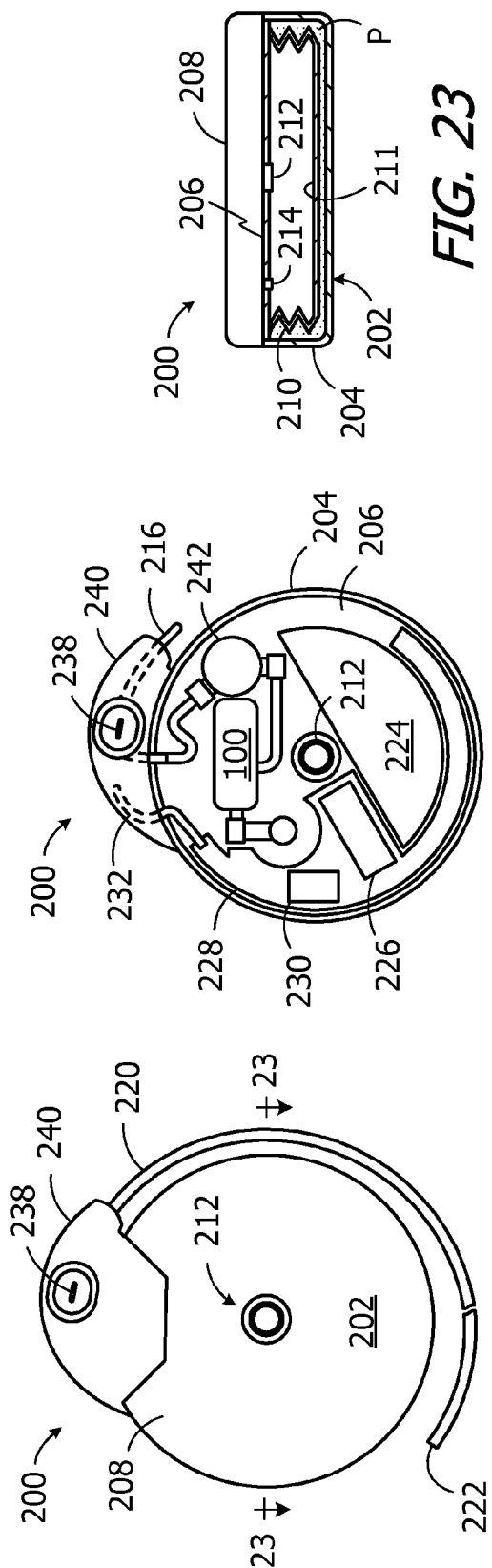
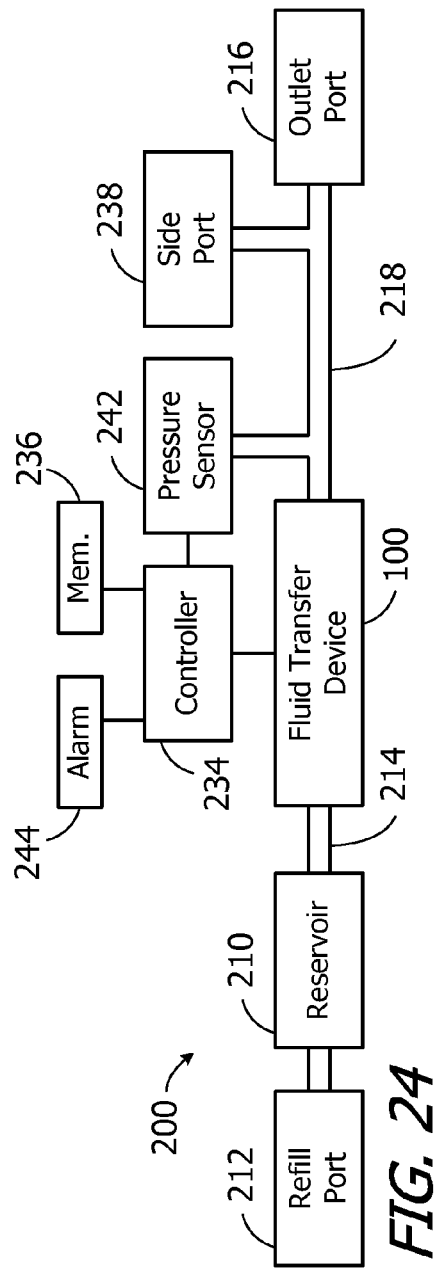

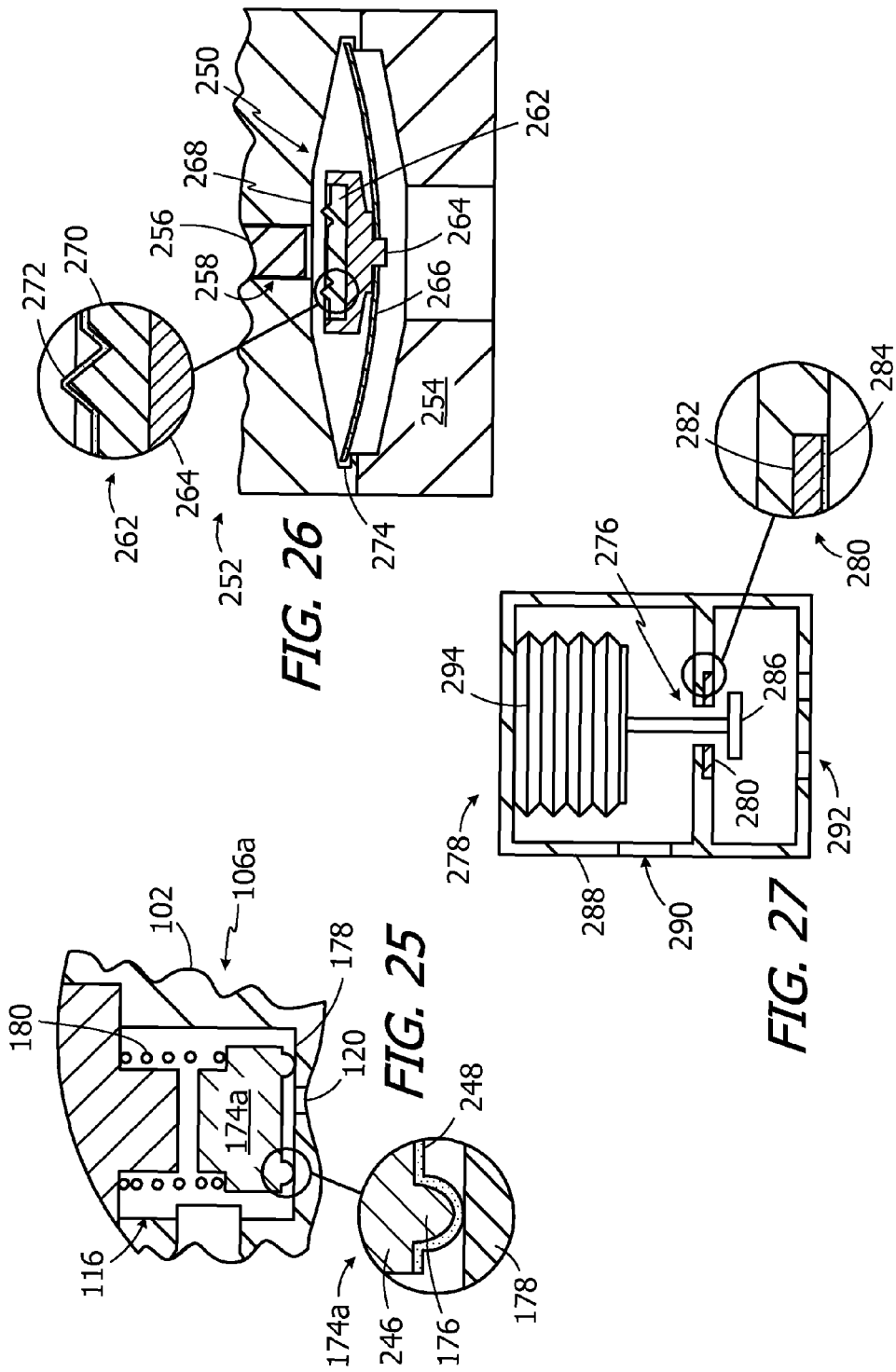

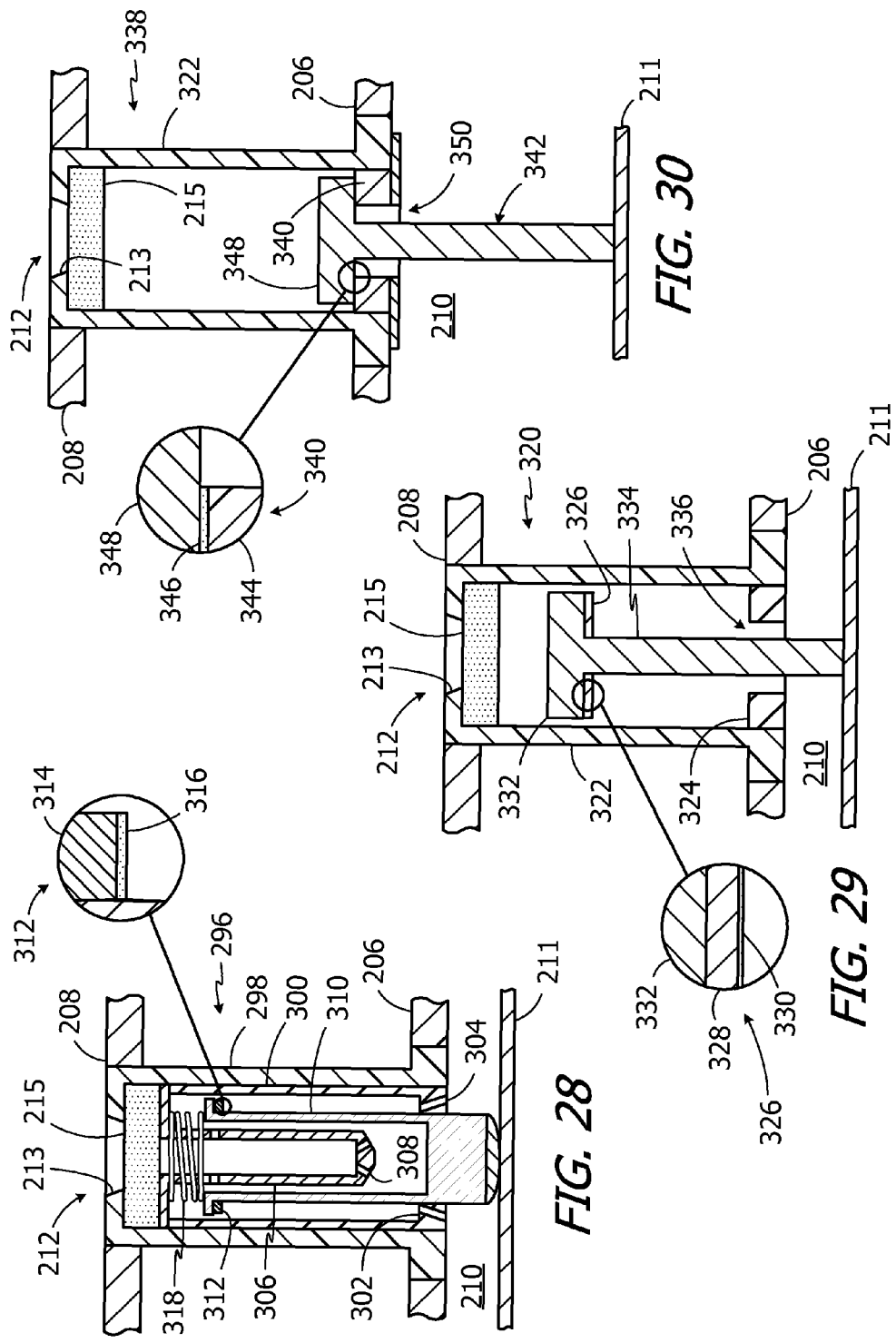

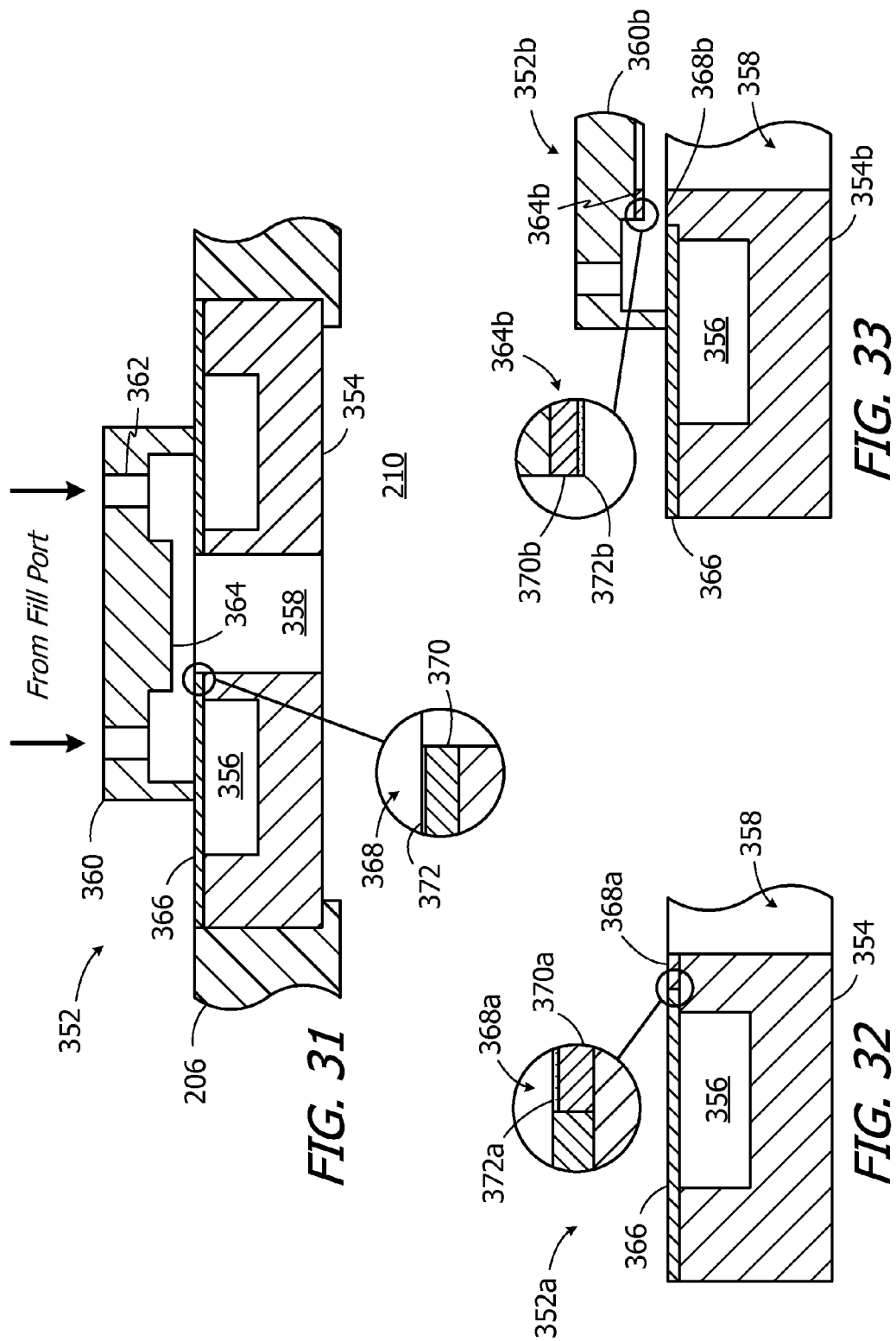

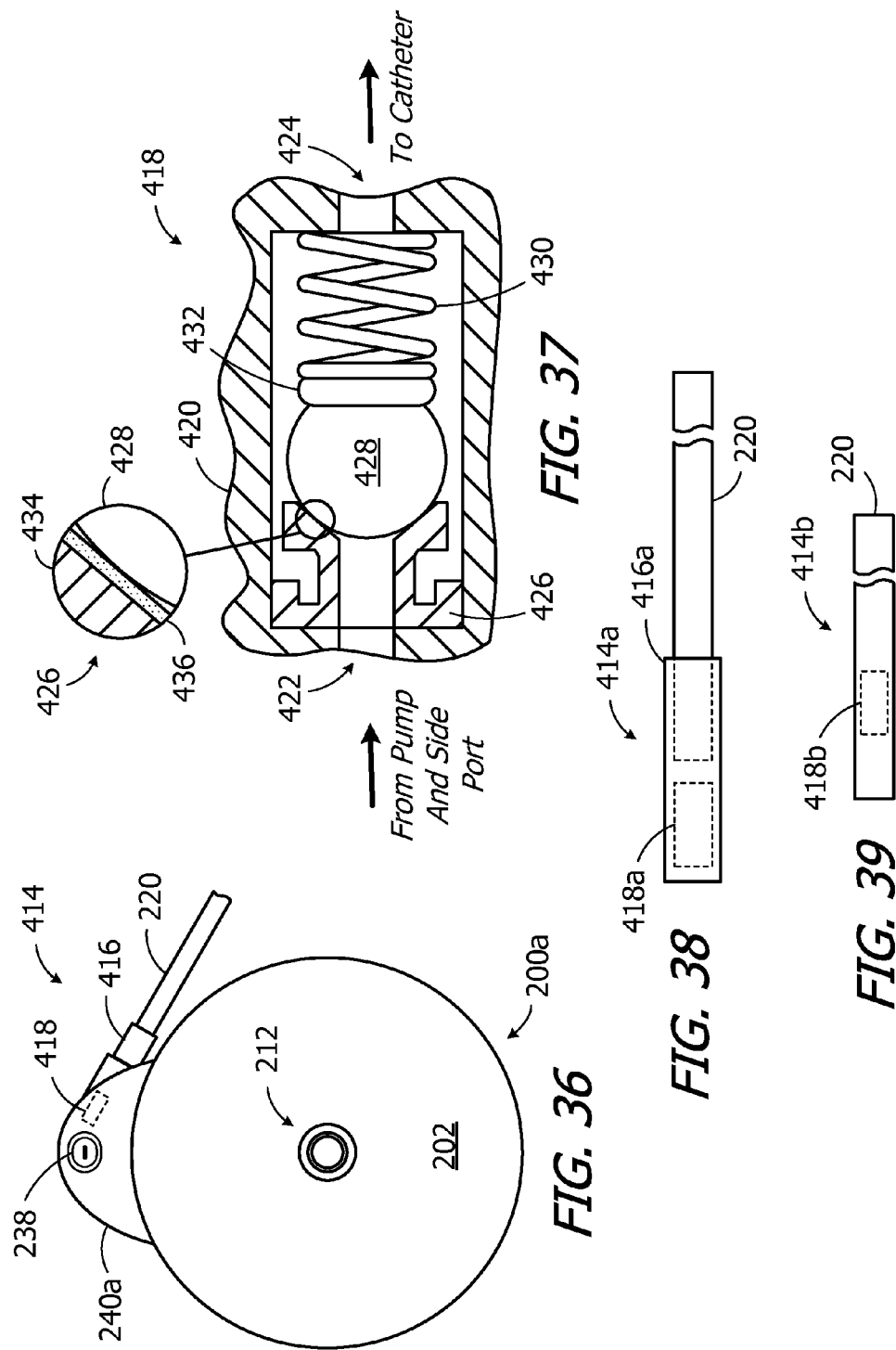

VALVES, VALVED FLUID TRANSFER DEVICES AND AMBULATORY INFUSION DEVICES INCLUDING THE SAME

CROSS-REFERENCE TO RELATED APPLICATION

This application is a continuation of U.S. application Ser. No. 14/049,076, filed Oct. 8, 2013, now U.S. Pat. No. 8,936,580, which is a continuation of U.S. application Ser. No. 13/594,737, filed Aug. 24, 2012, now U.S. Pat. No. 8,551,055, which is a continuation of U.S. application Ser. No. 12/054,009, filed Mar. 24, 2008, now U.S. Pat. No. 8,251,960, which claims the benefit of U.S. Provisional Application Ser. No. 60/896,910, filed Mar. 24, 2007 and entitled "Valves, Valved Fluid Transfer Devices and Ambulatory Infusion Devices Including The Same," which is incorporated herein by reference in its entirety.

BACKGROUND OF THE INVENTIONS

1. Field of Inventions

The present inventions relate generally to valve seats, valves, valved fluid transfer devices and ambulatory infusion devices including the same.

2. Description of the Related Art

Ambulatory infusion devices, such as implantable infusion devices and externally carried infusion devices, have been used to provide a patient with a medication or other substance (collectively "infusible substance") and frequently include a reservoir and a fluid transfer device. The reservoir is used to store the infusible substance and is coupled to the fluid transfer device which is, in turn, connected to an outlet port. A catheter, which has at least one outlet at the target body region, may be connected to the outlet port. As such, infusible substance in the reservoir may be transferred from the reservoir to the target body region by way of the fluid transfer device and catheter.

The fluid transfer devices in ambulatory infusion devices frequently include a pump, such as an electromagnet pump, and one or more valves. The present inventors have determined that the valves employed in such fluid transfer devices are susceptible to improvement. For example, the present inventors have determined that the main check valves are susceptible to improvement. Main check valves typically include a valve seat and a valve element that is movable relative to the valve seat. The valve element moves between a closed position where the valve element engages and compresses the valve seat, and an open position where the valve element is spaced from the valve seat. The present inventors have determined that adhesion of the valve element to the valve seat, including an increase in adhesion over time in normally closed valves, can reduce the effectiveness of the fluid transfer device by increasing the threshold force required to open the valve. Increasing the threshold force required to open the valve will, in turn, increase the load on the battery and may reduce the amount of fluid that flows through the valve during each pump cycle. The adhesion may also reduce the life of the valve seat itself. The present inventors have also determined that adhesion, including an increase in adhesion over time in normally closed valves, can reduce the effectiveness of other types of valves that may be associated with implantable infusion devices (e.g. bypass valves, outlet valves, pressure regulator valves, fill port valves, valves that employ a reference pressure, header assembly valves, and valves that are associated with catheters).

BRIEF DESCRIPTION OF THE DRAWINGS

Detailed descriptions of exemplary embodiments will be made with reference to the accompanying drawings.

FIG. 6 is a plan view of a valve seat in accordance with one embodiment of a present invention.

FIG. 7 is a section view taken along line 7-7 in FIG. 6.

FIG. 8 is a plan view of a valve seat in accordance with one embodiment of a present invention.

FIG. 9 is a section view taken along line 9-9 in FIG. 8.

FIG. 21 is a plan view of an implantable infusion device in accordance with one embodiment of a present invention.

FIG. 22 is a plan view of the implantable infusion device illustrated in FIG. 20 with the cover removed.

FIG. 23 is a partial section view taken along line 23-23 in FIG. 21.

FIG. 24 is a block diagram of the implantable infusion device illustrated in FIGS. 21-23.

FIG. 25 is a section view of a bypass valve in accordance with one embodiment of a present invention.

FIG. 26 is a section view of an outlet valve in accordance with one embodiment of a present invention.

FIG. 27 is a partial section view of a pressure regulator in accordance with one embodiment of a present invention.

FIG. 28 is a partial section view of a fill port in accordance with one embodiment of a present invention.

FIG. 29 is a partial section view of a fill port in accordance with one embodiment of a present invention.

FIG. 30 is a partial section view of a fill port in accordance with one embodiment of a present invention.

FIG. 31 is a section view of a pressure control valve in accordance with one embodiment of a present invention.

FIG. 32 is a section view of a portion of a pressure control valve in accordance with one embodiment of a present invention.

FIG. 33 is a section view of a portion of a pressure control valve in accordance with one embodiment of a present invention.

FIG. 36 is a plan view of an implantable infusion device in accordance with one embodiment of a present invention.

FIG. 37 is a partial section view of a portion of a catheter assembly in accordance with one embodiment of a present invention.

FIG. 38 is a plan view of a catheter assembly in accordance with one embodiment of a present invention.

FIG. 39 is a plan view of a catheter assembly in accordance with one embodiment of a present invention.

DETAILED DESCRIPTION OF THE EXEMPLARY EMBODIMENTS

Figure 1:
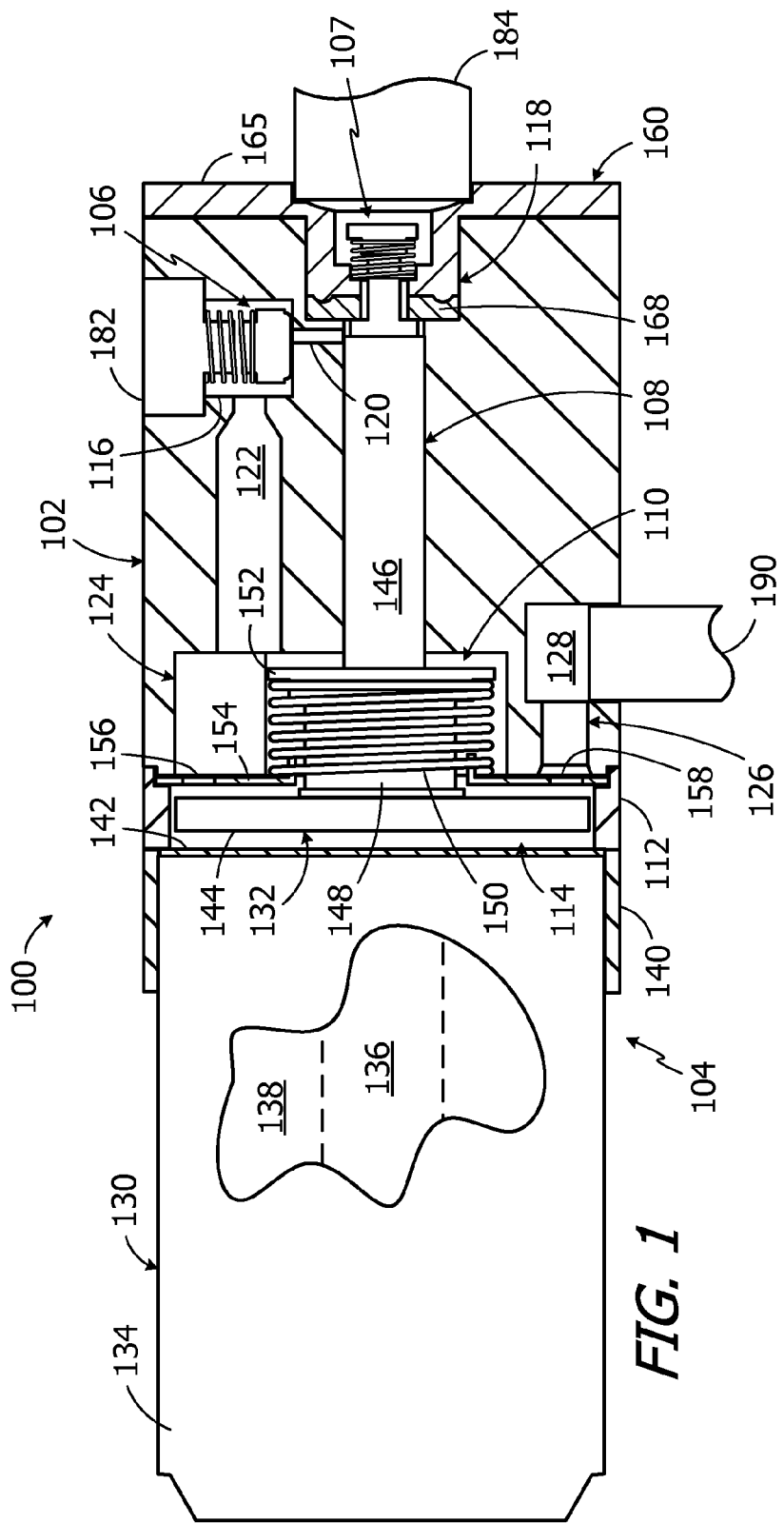
FIG. 1 is a side, partial section view of a fluid transfer device in accordance with various embodiments of some of the present invention.

The following is a detailed description of the best presently known modes of carrying out the inventions. This description is not to be taken in a limiting sense, but is made merely for the purpose of illustrating the general principles of the inventions. The present inventions have application in a wide variety of apparatus. One example is an electromagnet-pump-based fluid transfer device that may be employed in an implantable infusion device, and some of the present inventions are discussed in the context of electromagnet-pump-based fluid transfer devices and implantable infusion devices. The present inventions are not, however, limited to electromagnet-pump-based fluid transfer devices and implantable infusion devices and are instead also applicable to other fluid transfer devices and infusion devices that currently exist, or are yet to be developed. For example, the present inventions are applicable to fluid transfer devices with solenoid pumps, piezoelectric pumps, and any other mechanical or electromechanical pulsatile pump, as well as to externally carried infusion devices.

One example of a fluid transfer device is illustrated in FIGS. 1-5. The exemplary fluid transfer device, which is generally represented by reference numeral 100, includes a housing 102, an electromagnet pump 104, a bypass valve 106 and a main check valve 107. The valves 106 and 107 are in fluidic communication with the pump 104. The housing 102 in the exemplary fluid transfer device 100 is a generally solid, cylindrical structure with various open regions. The open regions accommodate portions of structures, such as the electromagnet pump 104, bypass valve 106, main check valve 107, and also define a fluid flow path. More specifically, the housing 102 includes a piston bore 108 and a hub recess 110 that respectively receive the electromagnet pump armature piston 146 and armature hub 148 (discussed below). A weld ring 112, which is secured to the end of the housing 102 opposite the main check valve 107, defines a pole recess 114 for the armature pole 144 (discussed below). A pair of valve recesses 116 and 118 for the bypass valve 106 and main check valve 107 are also provided. With respect to the fluid flow path, the housing 102 includes an orifice 120 that extends from the piston bore 108 to the bypass valve recess 116, a bypass fluid chamber 122, fluid passages 124 and 126, and an outlet recess 128. Additionally, and although it is not limited to any particular material(s), the exemplary housing 102 is formed from titanium.

Turning to the pump portion of the exemplary fluid transfer device 100, the electromagnet pump 104 includes an electromagnet 130 and an armature 132. The electromagnet 130, which is carried within in a case 134, includes a core 136 and a coil 138. The case 134 and core 136 are made from a magnetic material. The coil 138 consists of a wire or other conductor that is wound around the core 136. The coil 138 may be insulated from the case 134 by electrically non-conductive spacers (not shown), which center the coil within the case, or through the use of potting compound or encapsulant material between the case and the coil.

The electromagnet case 134 is secured to the housing 102 in the exemplary fluid transfer device 100 through the use of the aforementioned weld ring 112 on the housing and a weld ring 140 on the case. More specifically, the outer diameters of the weld rings 112 and 140 are substantially equal to one another and the outer surfaces thereof are substantially flush. During assembly, the housing 102 and the electromagnet case 134 are positioned on opposite sides of a barrier 142 and are then secured to one another by a weld (not shown) joining the outer surfaces of the weld rings 112 and 140. The barrier separates the pole recess 114, which will ultimately be filled with fluid, from the electromagnet 130.

The armature 132 in the illustrated embodiment is positioned within a fluid containing region of the housing that is defined by the piston bore 108, the hub recess 110 and the pole recess 114. The exemplary armature 132 consists of a pole 144 formed from a magnetic material (e.g. magnetic steel), which is located within the pole recess 114 such that it will be magnetically attracted to the electromagnet 130 when the electromagnet is actuated, and a cylindrically-shaped piston 146 that extends from the pole and through the piston bore 108 to the main check valve 107. A hub 148 is located within the hub recess 110 and is used to secure the pole 144 to the piston 146. A main spring 150 biases the armature 132 to the "rest" position illustrated in FIG. 1. The main spring 150 is compressed between a spring retainer 152 on the hub 148 and a spring retainer plate 154. The spring retainer plate 154, which is held in place by the housing 102 and the weld ring 112, includes an inlet opening 156 that allows fluid to pass from the fluid passage 124 to the pole recess 114 and an outlet opening 158 that allows fluid to pass from the pole recess to the fluid passage 126.

Figure 2:
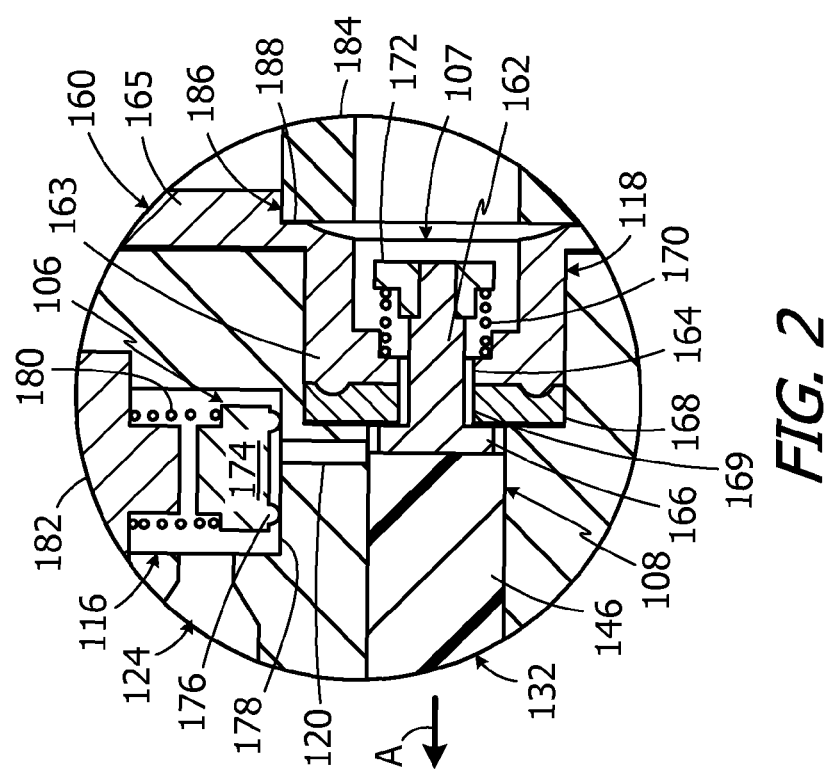
Figure 4:
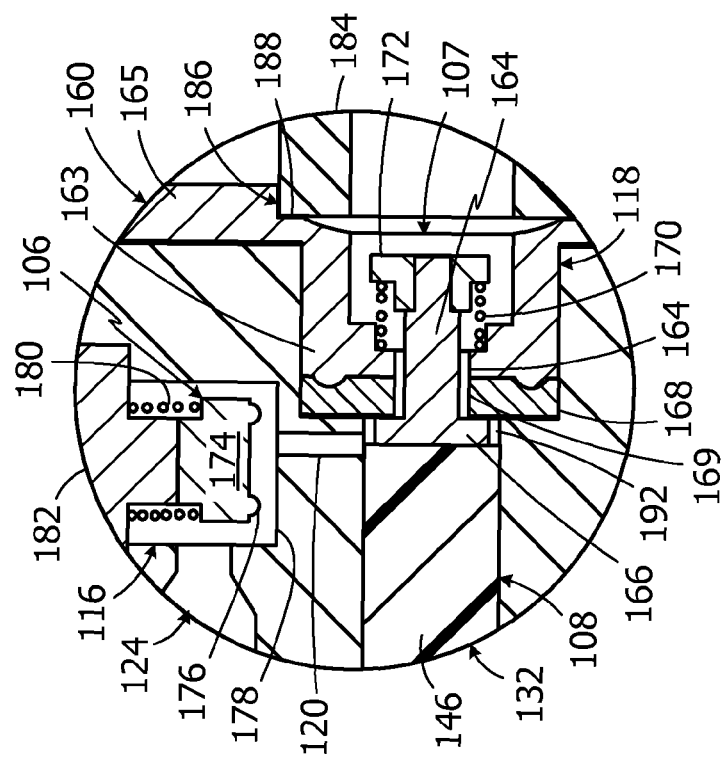
Figure 5:
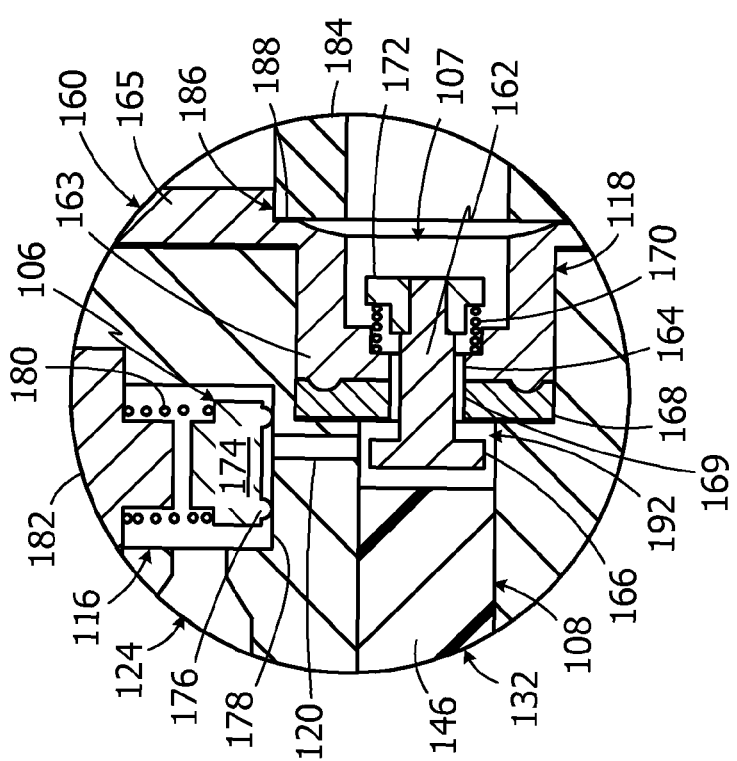

Turning to FIG. 2, the main check valve 107 includes a housing 160, which may be positioned within the valve recess 118 and secured to the housing 102, and a valve element (or "plunger") 162 that is movable relative to the housing 160. The exemplary housing 160 has a generally cylindrical fluid flow portion 163, with a fluid lumen 164 that is opened and closed by the valve element 162, and a mounting portion 165 that is used to secure the main check valve 107 to a fluid transfer device or other structure. In the illustrated embodiment, which is configured for use with a cylindrical fluid transfer device, the mounting portion 165 is disk-shaped. In other embodiments, the mounting portion 165 may be resized, reshaped or omitted altogether. The valve element 162 includes a head 166 that abuts an elastomeric valve seat 168 when the main check valve 107 is in the closed state illustrated in FIG. 2. The shaft portion of the valve element 162 passes through an opening 169 in the valve seat 168. The valve element 162 is biased to the closed position by a spring 170 (e.g. a coil spring) or other suitable biasing device. One end of the spring 170 abuts the housing 160 and the other end abuts a spring retainer 172 that is secured to the valve element 162. The exemplary valve seat 168, and other exemplary valve seats, are discussed in greater detail below in the context of FIGS. 6 and 19.

With respect to manufacturing and materials, the housing 160 in the exemplary main check valve 107 is a machined part and suitable materials for the housing include, but are not limited to, titanium, titanium alloys, stainless steel (e.g. 316L stainless steel), cobalt-nickel alloys, and refractory metals such as tantalum. The valve element 162 may also be machined and suitable materials for the machined valve element include, but are not limited to, those described above in the context of the housing 160. Alternatively, the valve element 162 may be molded and suitable materials for a molded valve element include, but are not limited to, polyolefins, liquid crystal polymers, PEEK, polyacetal plastics such as Delrin®, fluoropolymers, and most other molded materials that are rigid and inert to pharmaceuticals.

With respect to the bypass valve, the exemplary bypass valve 106 illustrated in FIG. 2 includes a valve element 174 with an integral sealing ring 176. The sealing ring 176, which has a semi-circular cross-sectional shape, engages the wall (or "seat") 178 that defines the end of the valve recess 116 and surrounds the orifice 120 when in the closed position illustrated in FIG. 2. Otherwise identical valve elements without the sealing ring may also be employed in the bypass valve. Suitable materials for the valve element 174 include elastomers such as, for example, silicone rubber, latex rubber, fluoropolymers, urethane, butyl rubber, and isoprene. In other implementations, the valve element 174 may be formed in whole or in part from a metal. The valve element 174 is biased to the closed position by a spring 180. One end of the spring 180 abuts the valve element 174, while the other end abuts a plug 182 that may be secured to housing 102 to maintain the bypass valve 106 within the valve recess 116. The plug 182 also forms a fluid tight seal which prevents fluid from escaping from the housing 102 by way of the valve recess 116.

Fluid may be supplied to the exemplary fluid transfer device 100 illustrated in FIG. 1 by way of an inlet tube 184. To that end, and referring to FIG. 2, the main check valve housing 160 includes a recess 186, with a shoulder 188, that receives the inlet tube 184. A filter (not shown) may be positioned within the recess 186 between the inlet tube 184 and the shoulder 188. The recess 186 and shoulder 188 may, alternatively, be associated with the fluid flow portion 163, or with both the fluid flow portion and the mounting portion 165, in other implementations of the main check valve 107. Fluid exits the fluid transfer device 100 by way of an outlet tube 190 (FIG. 1) that is received within the outlet recess 128 in the housing 102.

The exemplary fluid transfer device 100 operates as follows. Referring first to FIGS. 1 and 2, the fluid transfer device 100 is shown here in the "rest" state. The armature 132 is in the rest position, the electromagnet 130 is not energized, and the bypass valve 106 and main check valve 107 are both closed. Under normal operating conditions, there will be no flow through the fluid transfer device 100 when the fluid transfer device is in the rest state and the valves 106 and 107 are closed. Although sufficient pressure at the inlet tube 184 could result in the flow through the fluid transfer device 100 while the fluid transfer device is in the rest state illustrated in FIG. 2, the likelihood that this could occur is greatly reduced by maintaining the fluid source at a relatively low pressure.

The exemplary fluid transfer device 100 is actuated by connecting the coil 138 in the electromagnet 130 to an energy source (e.g. one or more capacitors that are being fired). The resulting magnetic field is directed through the core 136 and into, as well as through, the armature pole 144. The armature pole 144 is attracted to the core 136 by the magnetic field. The intensity of the magnetic field grows as current continues to flow through the coil 138. When the intensity reaches a level sufficient to overcome the biasing force of the main spring 150, the armature 132 will be pulled rapidly in the direction of arrow A (FIG. 2) until the armature pole 144 reaches the barrier 142. The armature piston 146 and hub 148 will move with armature pole 144 and compress the main spring 150. This is also the time at which fluid exits the fluid transfer device 100 by way of the passage 126 and the outlet tube 190.

Figure 3:
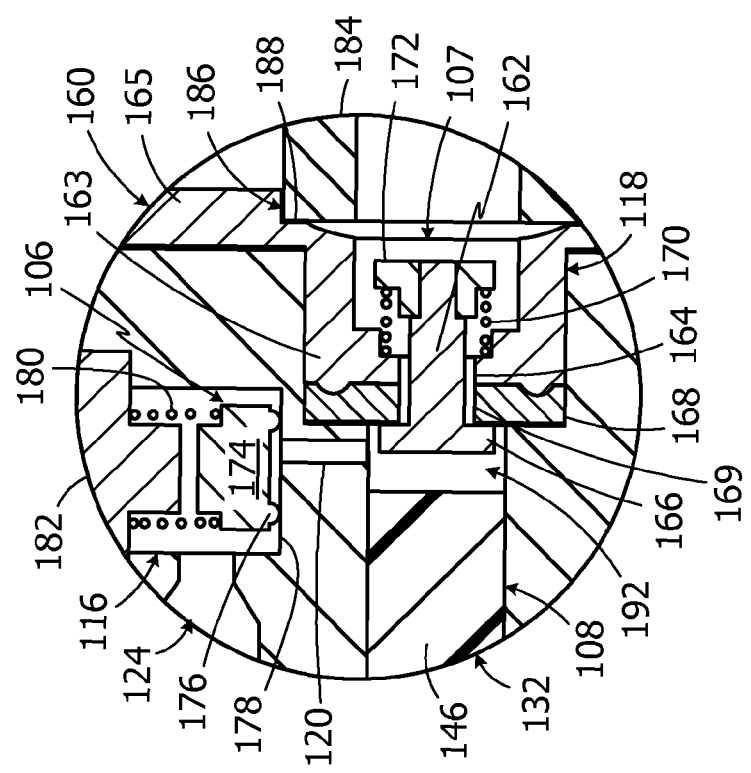
FIGS. 2-5 are section views showing the fluid transfer device illustrated in FIG. 1 in various states.

Movement of the armature piston 146 from the position illustrated in FIG. 2 to the position illustrated in FIG. 3 results in a decrease in pressure in the pump chamber 192, i.e. the volume within the piston bore 108 between the armature piston 146 and the valve seat 168. The coil will continue to be energized for a brief time (e.g. a few milliseconds) in order to hold the armature piston 146 in the location illustrated in FIG. 3. The reduction in pressure within the pump chamber 192 will open the main check valve 107 by overcoming the biasing force of the spring 170 and move valve element 162 to the position illustrated in FIG. 4. As a result, the valve head 166 will move away from the valve seat 168 and fluid will flow into the pump chamber 192. The main check valve 107 will close, due to the force exerted by spring 170 on valve element 162, once the pressure within pump chamber 192 is equal to pressure at the inlet tube 184. However, because the coil 138 continues to be energized, the armature 132 will remain in the position illustrated in FIGS. 3 and 4 as fluid flows into the pump chamber 192 and the main check valve 107 closes.

Immediately after the main check valve 107 closes, the coil 138 will be disconnected from the energy source and the magnetic field established by the electromagnet 130 will decay until it can no longer overcome the force exerted on the armature 132 by the main spring 150. The armature 132 will then move back to the position illustrated in FIGS. 2 and 5. The associated increase in pressure within the pump chamber 192 is sufficient to open the bypass valve 106 by overcoming the biasing force of the spring 180 and moving the valve element 174 to the position illustrated in FIG. 5. The increase in pressure within the pump chamber 192, coupled with movement of the valve element away from the wall 178, results in the fluid flowing through the orifice 120 to the fluid chamber 122. The flow of fluid will cause the pressure in the orifice 120 and the fluid chamber 122 to equalize. At this point, the bypass valve 106 will close, due to the force exerted by spring 180 on the valve element 174, thereby returning the exemplary fluid transfer device 110 to the rest state illustrated in FIG. 2.

Additional general information concerning the exemplary fluid transfer device 100, as well as other fluid transfer devices, may be found in U.S. Pat. Nos. 6,227,818 and 6,264,439 and U.S. Patent Pub. No. 2007/0269322.

As alluded to above, the present inventors have determined that adhesion of a valve element to a valve seat, including an increase in adhesion over time in normally closed valves, can reduce the effectiveness of the fluid transfer device by increasing the threshold force required to open the main check valve and, in turn, increasing the load on the battery and reducing the amount of fluid that flows through the valve during each pump cycle. Such adhesion may also reduce the life of the valve seat. The present valve seats are configured to provide the same biocompatibility and sealing capabilities as conventional valves seats, i.e. maintain a seal over a million or more open/close cycles and take a minimal compression set, in a manner that results in less adhesion of the valve seat to the valve element. To that end, the present valve elements include a main portion and a seal portion (or "non-stick portion") that is configured to be less tacky than the main portion. As used herein, a "less tacky" seal portion results in a lower adhesion between the valve seat and valve element (sometimes referred to as "pull-off adhesion"), after the same contact time and pressure, than an overall identically shaped valve seat that includes seal portion that is not configured to be less tacky. For example, the main portion, which is majority of the present valve seats, may be formed from a material that provides the requisite sealing capabilities and the seal portion, which will contact the valve element when the valve is closed, may be formed from a material that is less tacky than the material that forms the main portion. The seal portion may, alternatively, be a surface of the main portion that has been treated in such a manner that it is less tacky than it was prior to the treatment.

Figure 19:
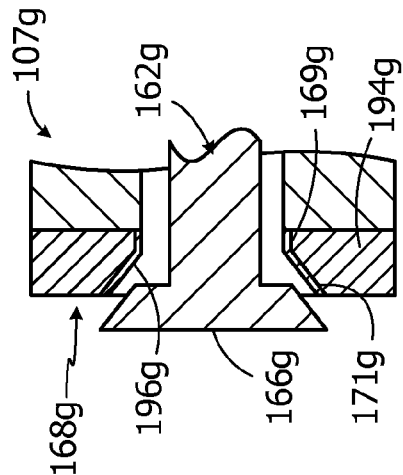
FIG. 19 is section view of a portion of a valve in accordance with one embodiment of a present invention.

Valve seats in accordance with the present inventions may have any overall shape and cross-sectional shape that is required for the associated valve. The valve seats illustrated in FIGS. 6-17, for example, have annular overall shapes and are rectangular in cross-section. Other exemplary shapes are illustrated in FIGS. 18 and 19.

The overall dimensions of the present main check valves and the elements thereof will, of course, depend upon the particulars of the valve and the associated fluid transfer device. In the exemplary context of implantable drug delivery devices, and although the volume/stroke magnitude may be increased in certain situations, the fluid transfer devices will typically deliver about 1 microliter/stroke, but may be more or less (e.g. about 0.25 microliter/stroke or less) depending on the particular fluid transfer device employed. One implementation of such a fluid transfer device, the housing 102 will be about 10 mm long and about 7.5 mm in diameter, and the armature piston 146 will be about 1.25 mm in diameter. The main check valve 107 associated with such a fluid transfer device may have the following dimensions. The diameters of the housing fluid flow portion 163 and the mounting portion 165 are about 2.5 mm and about 7.5 mm, respectively. The length of the valve 107, i.e. the combined lengths of the fluid flow portion 163 and the mounting portion 165 plus the thickness of the valve seat 168, is about 2.5 mm. The outer diameter of the valve seat 168 will be about 2.5 mm, the inner diameter will be about 1 mm and the thickness will be about 0.25 mm. The pull-off adhesion of the seal portion in some embodiments will be less than about 0.5 psi in those instances where the valve seat opening is about 0.040 inch.

Referring first to FIGS. 6 and 7, the exemplary valve seat 168 has a main portion 194 and a seal portion 196. The seal portion 196 is the portion that is engaged by a portion of the valve element (e.g. valve element head 166) when the main check valve is closed. Suitable materials for the main portion 194 include, but are not limited to, silicone rubber, latex rubber, fluoropolymers, urethane, butyl rubber, and isoprene. Such materials allow the valve seat 168 to maintain a seal over a million or more open/close cycles and take a minimal compression set. The seal portion 196 is a layer of silicon suboxide ($SiO_xC_y$, where x<2 and y<1) such as, for example, $SiO_{1.7}C_{0.4}$. The seal portion 196 is relatively thin and plasma deposition (or other suitable techniques) may be used to deposit the silicon suboxide onto the main portion 194. The thickness of a relatively thin layer of silicon suboxide is about 0.1 μm to about 10 μm, and the seal portion 196 in the illustrated embodiment is about 0.3 μm to about 0.8 μm thick. The seal portion 196 may also cover the entire top surface of the main portion 194 (as shown), only that part of the main portion top surface that would otherwise be engaged by the valve element head 166, or something in between.

The seal portion 196 may, in other implementations, be a layer of $SiO_2$ that is about 0.1 μm to about 10 μm thick and formed by an oxygenated plasma treatment of the main portion 194.

Another exemplary valve seat that may be included in a main check valve (e.g. main check valve 107) is generally represented by reference numeral 168a in FIGS. 8 and 9. The exemplary valve seat 168a has a main portion 194a and a seal portion 196a. The seal portion 196a is the portion that is engaged by a portion of the valve element (e.g. valve element head 166) when the main check valve is closed. Suitable materials for the main portion 194 include, but are not limited to, elastomers such as silicone rubber, latex rubber, fluoropolymers, urethane, butyl rubber, and isoprene. Such materials allow the valve seat 168a to maintain a seal over a million or more open/close cycles and take a minimal compression set. The seal portion 196a is a layer of a relatively hard durometer of the same class of material that is used to form the main portion 194a. As used in this context, a relatively hard material is a material that is at least 50% harder than the material to which it is being compared. For example, if the main portion 194a is formed from a silicone rubber that has a hardness of about 40 Shore A, then the seal portion 196a may be formed from silicone rubber that has a hardness of about 60-80 Shore A. Alternatively, instead of a relatively hard durometer of the same class of material, a relatively hard durometer of one of the other main portion elastomers listed above may be used. The seal portion 196a may be relatively thin and formed by plasma deposition, vapor deposition, chemical modification, comolding, dip coating, or spin coating. The thickness of a relatively thin layer of a relatively hard elastomer is about 0.001 mm to about 0.05 mm (e.g. about 0.001 mm if plasma deposited, about 0.025 mm if spin coated, and about 0.05 mm if comolded or dip coated), and the seal portion 196a in the illustrated embodiment is about 0.05 mm thick. The seal portion 196a may cover the entire top surface of the main portion 194a (as shown), only that part of the main portion top surface that would otherwise be engaged by the valve element head 166, or something in between.

Figure 11:
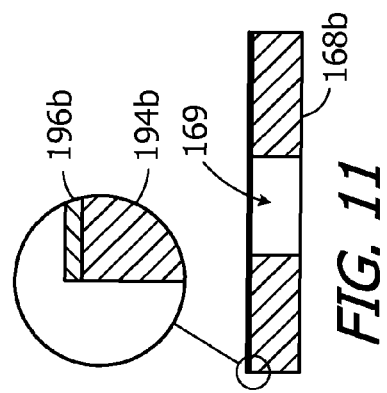
FIG. 11 is a section view taken along line 11-11 in FIG. 10.
Figure 10:
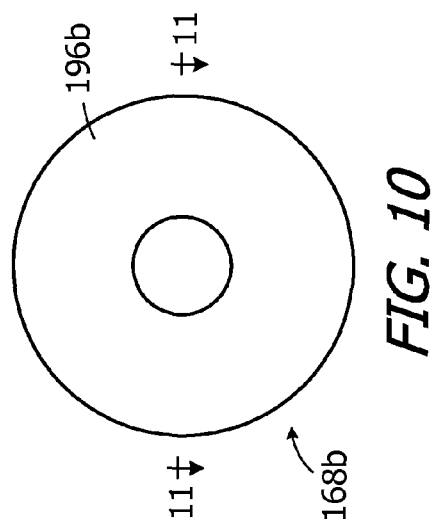
FIG. 10 is a plan view of a valve seat in accordance with one embodiment of a present invention.

Turning to FIGS. 10 and 11, another exemplary valve seat that may be included in a main check valve (e.g. main check valve 107) is generally represented by reference numeral 168b. The exemplary valve seat 168b has a main portion 194b and a seal portion 196b. The seal portion 196b is the portion that is engaged by a portion of the valve element (e.g. valve element head 166) when the main check valve is closed. Suitable materials for the main portion 194b include, but are not limited to, elastomers such as silicone rubber, latex rubber, fluoropolymers, urethane, butyl rubber, and isoprene. Such materials allow the valve seat 168b to maintain a seal over a million or more open/close cycles and take a minimal compression set. The seal portion 196b is a layer of material with a hardness that is the same as, or is at least relatively close to (i.e. within 30%), the material that forms the main portion 194b, but that is less tacky than the material that forms the main portion. For example, if the main portion 194b is formed from a silicone rubber that is about 40 Shore A hardness, then the seal portion 196b may be formed from, for example, a fluoroelastomer or a low friction (or "non-stick") protective coating that is designed for use with silicone (e.g. a silicone coating polymer filled with particles such as that sold under the trade name TopCoat) that has a hardness of about 40 Shore A. Other exemplary materials include aluminum oxide, silicone- or silane-based coatings from NuSil Technologies LLC, titanium oxide, carbon (including carbon in the form of diamond or graphite), parylene, fluorosilicone, perfluorosilicone, ethylene propylene diene monomer (EPDM) rubber, halogenated rubber such as bromo/chlorobutyl rubber, and polyisobutylene thermoplastic. The seal portion 196b may be relatively thin and formed by spray coating, spin coating, or dip coating. The thickness of a relatively thin layer of a less tacky layer (e.g. a fluoroelastomer or a low friction coating) is about 0.01 mm to about 0.05 mm, and is about 0.025 mm thick in the illustrated embodiment. The seal portion 196b may cover the entire top surface of the main portion 194b (as shown), only that part of the main portion top surface that would otherwise be engaged by the valve element head 166, or something in between.

A layer that is less tacky than a silicone main portion 194b may also be formed by treating the silicone main portion with a lubricating agent such as MDX4-4120 from Dow Corning or fluoro oil. These lubricating agents absorb into the silicone to form a less tacky layer that defines the seal portion 196b.

Figure 13:
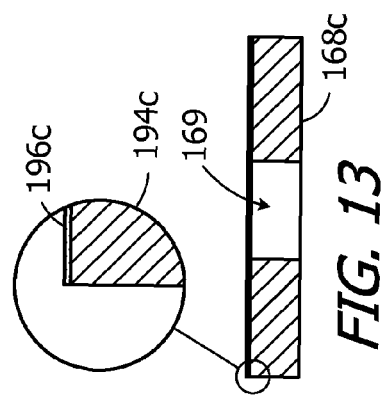
FIG. 13 is a section view taken along line 13-13 in FIG. 12.
Figure 12:
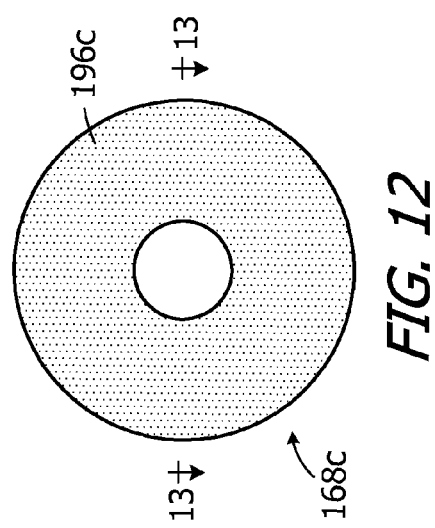
FIG. 12 is a plan view of a valve seat in accordance with one embodiment of a present invention.

Another exemplary valve seat that may be included in a main check valve (e.g. main check valve 107) is generally represented by reference numeral 168c in FIGS. 12 and 13. The exemplary valve seat 168c has a main portion 194c and a seal portion 196c. The seal portion 196c is the surface that is engaged by a portion of the valve element (e.g. valve element head 166) when the main check valve is closed. Suitable materials for the main portion include, but are not limited to, elastomers such as silicone rubber, latex rubber, fluoropolymers, urethane, butyl rubber, and isoprene. Such materials allow the valve seat 168c to maintain a seal over a million or more open/close cycles and take a minimal compression set. The seal portion 196c is a halogenated surface of the main portion 194c and the halogenated surface is less tacky than the material which forms the main portion. The seal portion 196c (or "halogenated surface") is formed by treating a surface of the main portion with a halogen such as, for example, chlorine, fluorine or bromine. The thickness of the halogen may be, for example, about 1 molecular layer (e.g. about 0.1 to about 1 nanometers). The seal portion 196c may cover the entire top surface of the main portion 194c (as shown), only that part of the main portion top surface that would otherwise be engaged by the valve element head 166, or something in between.

Figure 15:
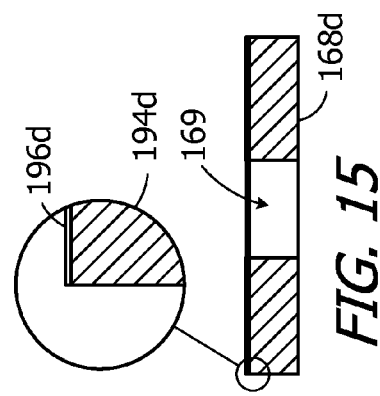
FIG. 15 is a section view taken along line 15-15 in FIG. 14.
Figure 14:
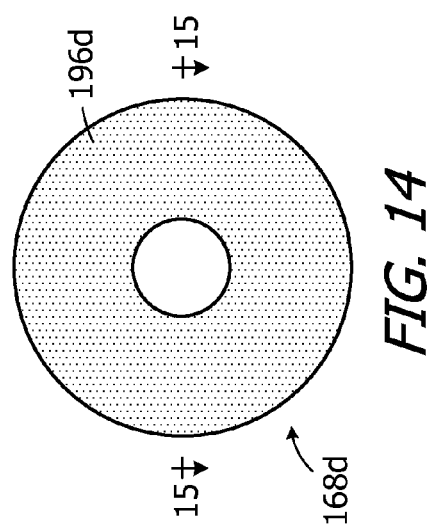
FIG. 14 is a plan view of a valve seat in accordance with one embodiment of a present invention.

Turning to FIGS. 14 and 15, another exemplary valve seat that may be included in a main check valve (e.g. main check valve 107) is generally represented by reference numeral 168d. The exemplary valve seat 168d has a main portion 194d and a seal portion 196d. The seal portion 196d is the surface that is engaged by a portion of the valve element (e.g. valve element head 166) when the main check valve is closed. Suitable materials for the main portion include, but are not limited to, elastomers such as silicone rubber, latex rubber, fluoropolymers, urethane, butyl rubber, and isoprene. Such materials allow the valve seat 168d to maintain a seal over a million or more open/close cycles and take a minimal compression set. The seal portion 196d is an ion-implanted surface, or an ion-beam assisted ion-implanted/coated surface, of the main portion 194d and is less tacky than the main portion. The seal portion 196d (or "ion-implanted surface" or "ion-implanted/coated surface") is formed by ion-implanting a ceramic material (e.g. aluminum oxide), a metal material (e.g. titanium) or a metal-oxide (e.g. titanium dioxide) into a surface of the main portion. The implanted ions may be distributed randomly and interstitially (e.g. on the surface, below the surface, and partially implanted into the surface). It should be noted that, even if the ions are subsequently removed, the surface will be less tacky than it was prior to the treatment because the ion-implantation process changes the internal chemical structure in the silicone rubber or other elastomeric material that forms the main portion 194d. Alternatively, ion-implantation may be combined with a deposition step that first implants and then deposits a thin layer of the implanted material on top of the surface of the main portion. For example, a layer that is about 100 nanometers thick with an implantation depth of about 1 micron may be formed on the main portion 194d.

Figure 17:
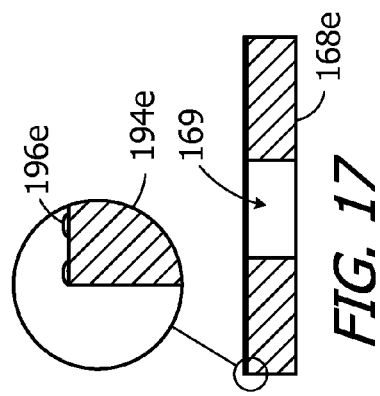
FIG. 17 is a section view taken along line 17-17 in FIG. 16.
Figure 16:
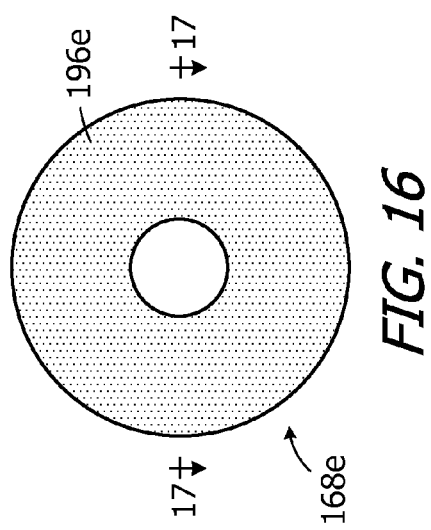
FIG. 16 is a plan view of a valve seat in accordance with one embodiment of a present invention.
Figure 18:
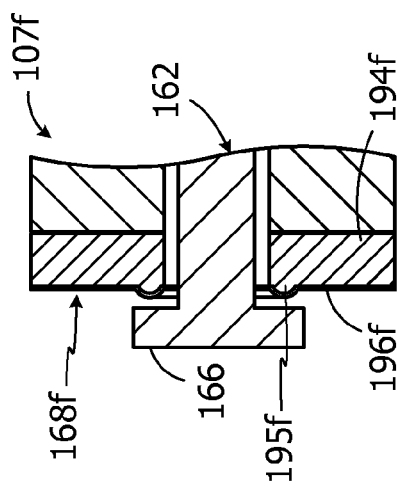
FIG. 18 is section view of a portion of a valve in accordance with one embodiment of a present invention.

Another exemplary valve seat that may be included in a main check valve (e.g. main check valve 107) is generally represented by reference numeral 168e in FIGS. 16 and 17. The exemplary valve seat 168e has a main portion 194e and a seal portion 196e. The seal portion 196e is the portion that is engaged by a portion of the valve element (e.g. valve element head 166) when the main check valve is closed. Suitable materials for the main portion include, but are not limited to, elastomers such as silicone rubber, latex rubber, fluoropolymers, urethane, butyl rubber, and isoprene. Such materials allow the valve seat 168e to maintain a seal over a million or more open/close cycles and take a minimal compression set. The seal portion 196e is a coating of a filler (e.g. fumed silica, ground mica, talc, Teflon®, $TiO_2$, barium sulfate, etc.) that reduces the contact area and surface interaction between the valve element and the tackier material (e.g. silicone rubber) which forms the main portion 194e. The seal portion 196e may be relatively thin and formed by comolding, plasma etching to expose the filler material on the surface, or applying a thin coating of the filled materials on an unfilled main portion. The thickness of a relatively thin layer of a filler is about 0.025 mm to about 0.075 mm thick, and in the illustrated embodiment, is about 0.05 mm thick. The seal portion 196e may cover the entire top surface of the main portion 194e (as shown) or only that portion of the main portion top surface that would otherwise be engaged by the valve element head 166.

As noted above, valve seats in accordance with the present inventions may have shapes other than the annular shape illustrated in FIGS. 6-17. For example, the exemplary valve seat 168f illustrated in FIG. 18 has a main portion 194f, with a raised area 195f, and a seal portion 196f. The raised area 195f, which is semi-circular in cross-section and circular in plan in the illustrated embodiment, reduces the contact area between valve seat 168f and the valve element head 166. This, in turn, increases the sealing pressure, as compared to a sealing arrangement with a flat valve head and a flat valve seat. Additionally, although the raised area 195f will flatten slightly when the main check valve 107f is closed, the curved raised area will reduce the amount of flat-on-flat surface area as well as the adhesion force associated therewith. The main portion 194f and seal portion 196f may be formed by the same materials, using the same manufacturing processes, as the main portions and seal portions described above in the context of FIGS. 6-17.

Another exemplary valve seat that does not have a purely annular shape is generally represented by reference numeral 168g in FIG. 19. The valve seat 168g, which includes a main portion 194g and a seal portion 196g, is configured to be incorporated into a low ullage valve 107g with a valve element 162g. The valve element 162g includes a head 166g that is shaped like a truncated cone, and the valve seat 168g includes a correspondingly shaped indentation 171g that extends to the valve seat opening 169g. Such shapes allow the valve element head 166g to nest in the valve seat 168g. The seal portion 196g is associated with the indentation and, depending on the manner in which the seal portion is produced, may also be associated with the opening 169g. The main portion 194g and seal portion 196g may be formed from the same materials, using the same manufacturing processes, as the main portions and seal portions described above in the context of FIGS. 6-17.

As illustrated above, the seal portions 196-196g each perform the function of making a surface of the associated valve seat less tacky than the material elastomeric material which forms the main portion 194-194g.

Figure 20:
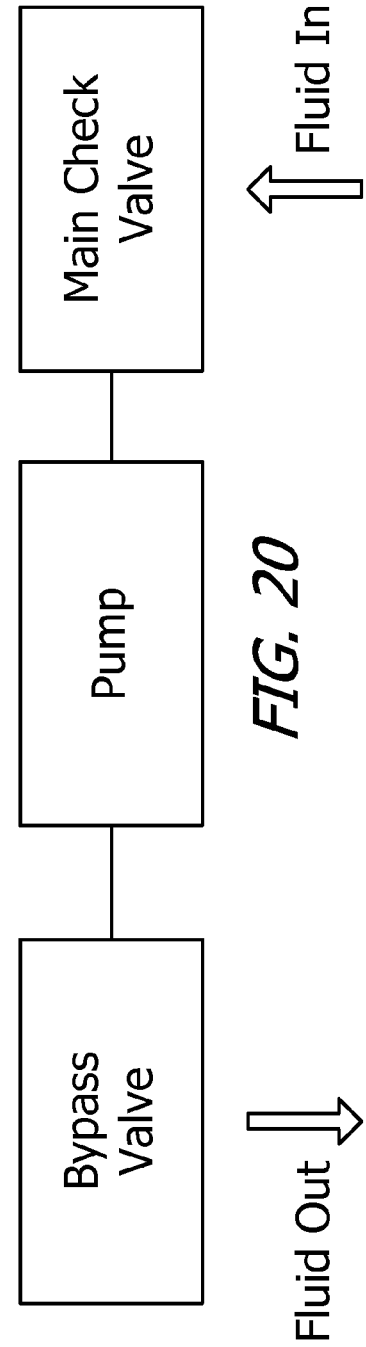
FIG. 20 is a block diagram of a fluid transfer device.

Referring to FIG. 20, and as discussed in detail above, fluid transfer devices in accordance with some of the present inventions may include a pump and a main check valve. The pump may be, by way of example but not limitation, an electromagnet pump, a solenoid pump, a piezoelectric pump, or any other mechanical or electromechanical pulsatile pump, the main check valve may be any of the main check valves described above and, accordingly, the present fluid transfer devices include any and all combinations of such pumps and main check valves. The present fluid transfer device may also include a bypass valve. One example of such a bypass valve is generally represented by reference numeral 106 in FIG. 1. Fluid entering such fluid transfer devices will typically pass the main check valve prior to being acted on by the pump, and will pass the bypass valve on its way to the outlet after being acted one by the pump.

One example of an implantable infusion device that may include any of the valve seats, valves and/or fluid transfer devices described above is generally represented by reference numeral 200 in FIGS. 21-24. As used herein, an "implantable infusion device" is a device that includes a reservoir and an outlet, and is sized, shaped and otherwise constructed (e.g. sealed) such that both the reservoir and outlet can be simultaneously carried within the patient's body. The exemplary infusion device 200 includes a housing 202 (e.g. a titanium housing) with a bottom portion 204, an internal wall 206, and a cover 208. An infusible substance (e.g. medication) may be stored in a reservoir 210 that is located within the housing bottom portion 204. The reservoir 210 may be replenished by way of a fill port 212 that extends from the reservoir, through the internal wall 206, to the cover 208. A hypodermic needle (not shown), which is configured to be pushed through the fill port 212, may be used to replenish the reservoir 210.

A wide variety of reservoirs may be employed. In the illustrated embodiment, the reservoir 210 is in the form of a titanium bellows with an end wall 211 that is positioned within a sealed volume defined by the housing bottom portion 204 and internal wall 206. The remainder of the sealed volume is occupied by propellant P, which may be used to exert negative pressure on the reservoir 210. Other reservoirs that may be employed in the present infusion devices include reservoirs in which propellant exerts a positive pressure. Still other exemplary reservoirs include negative pressure reservoirs that employ a movable wall that is exposed to ambient pressure and is configured to exert a force that produces an interior pressure which is always negative with respect to the ambient pressure.

The exemplary ambulatory infusion device 200 illustrated in FIGS. 21-24 also includes the fluid transfer device 100. The inlet of the fluid transfer device 100 is coupled to the interior of the reservoir 210 by a passageway 214, while the outlet of the fluid transfer device is coupled to an outlet port 216 by a passageway 218. Operation of the fluid transfer device 100 causes infusible substance to move from the reservoir 210 to the outlet port 216. A catheter 220 may be connected to the outlet port 216 so that the infusible substance passing through the outlet port will be delivered to a target body region in spaced relation to the infusion device 200 by way of the outlet(s) 222 at or near the end of the catheter.

Energy for the fluid transfer device 100, as well for other aspects of the exemplary infusion device 200, is provided by the battery 224 illustrated in FIG. 22. In the specific case of the fluid transfer device 100, the battery 224 is used to charge one or more capacitors 226, and is not directly connected to the fluid transfer device itself. The capacitor(s) 226 are connected to an electromagnet coil in the fluid transfer device 100, and disconnected from the battery 224, when the electromagnet coil is being energized, and are disconnected from the electromagnet coil and connected to the battery when the capacitor(s) are being recharged and/or when the fluid transfer device is at rest. The capacitor(s) 226 are carried on a board 228. A communication device 230, which is connected to an antenna 232, is carried on the same side of the board 228 as the capacitor(s) 226. The exemplary communication device 230 is an RF communication device. Other suitable communication devices include, but are not limited to, oscillating magnetic field communication devices, static magnetic field communication devices, optical communication devices, ultrasound communication devices and direct electrical communication devices.

A controller 234 (FIG. 24), such as a microprocessor, microcontroller or other control circuitry, is carried on the other side of the board 228. The controller controls the operations of the infusion device 200 in accordance with instructions stored in memory 236 and/or provided by an external device (e.g. a remote control programmer) by way of the communication device 230. For example, the controller 234 may be used to control the fluid transfer device 100 to supply fluid to the patient in accordance with, for example, a stored basal delivery schedule or a bolus delivery request. The controller 234 may also be used to monitor sensed pressure and perform the analytical functions described below.

Referring to FIGS. 21, 22 and 24, the exemplary infusion device 200 is also provided with a side port 238 that is connected to the passageway 218 between the outlet of the fluid transfer device 100 and the outlet port 216. The side port 238 facilitates access to an implanted catheter 220, typically by way of a hypodermic needle. For example, the side port 238 allows clinicians to push fluid into the catheter 220 and/or draw fluid from the catheter for purposes such as checking catheter patency, sampling CSF, injecting contrast dye into the patient and/or catheter, removing medication from the catheter prior to dye injection, injecting additional medication into the region at the catheter outlet 222, and/or removing pharmaceuticals or other fluids that are causing an allergic or otherwise undesirable biologic reaction.

The outlet port 216, a portion of the passageway 218, the antenna 232 and the side port 238 are carried by a header assembly 240. The header assembly 240 is a molded, plastic structure that is secured to the housing 202. The housing 202 includes a small aperture through which portions of the passageway 218 are connected to one another, and a small aperture through which the antenna 232 is connected to the board 228.

The exemplary infusion device 200 illustrated in FIGS. 21-24 also includes a pressure sensor 242 that is connected to the passageway 218 between the outlet of the fluid transfer device 100 and the outlet port 216. As such, the pressure sensor 242 senses the pressure at the outlet port 216 which, in the illustrated embodiment, is also the pressure within the catheter 220. The pressure sensor 242 is connected to the controller 234 and may be used to analyze a variety of aspects of the operation of the exemplary implantable infusion device 200. For example, pressure measurements may be used by the controller 234 to determine whether or not there is a blockage in the catheter 220 and whether or not the fluid transfer device 100 is functioning properly. The controller 234 may perform a variety of different functions in response to a determination that the fluid transfer device 100 is not functioning properly or a determination that the catheter 220 is blocked. For example, the controller 234 may actuate an audible alarm 244 that is located within the housing 202 in order to signal that the fluid transfer device 100 is not functioning properly or the catheter 220 is blocked.

The present inventions are also applicable to other types of valves. Referring first to FIG. 25, the exemplary bypass valve 106a is essentially identical to the bypass valve 106 and similar elements are represented by similar reference numerals. Here, however, the elastomeric valve element 174a includes a main portion 246 and a seal portion 248. The seal portion 248 may cover the entire surface of the main portion 246 that faces/engages the wall (or "seat") 178, as shown, or may merely cover the sealing ring 176. The main portion 246 and seal portion 248 may be formed from the same materials, using the same manufacturing methods, as the valve seat main portions 194-194g and seal portions 196-196g described above. The bypass valve 106a may be included in fluid transfer devices such as the exemplary fluid transfer device 100 and/or may be included in implantable infusion devices such as the implantable infusion device 200.

Another exemplary valve is the outlet valve 250 illustrated in FIG. 26, which is shown in its open position in a fluid transfer device 252 that includes a housing 254 and a pump with a piston 256 in a piston bore 258. The piston 256 is driven by an electromagnet and spring arrangement (not shown). The exemplary outlet valve 250, which is in fluidic communication with the pump, includes a housing which is incorporated into the housing 254, an elastomeric valve element 262, a valve element retainer 264, and a spring 266 that biases the valve element against the wall (or "seat") 268 which extends around the piston bore 258. The surface of the valve element 262 that engages the wall 268 may be uneven, as shown, flat, or any other suitable shape. The valve element 262 also includes a main portion 270 and a seal portion 272. The valve element main portion 246 and seal portion 248 may be formed from the same materials, using the same manufacturing methods, as the valve seat main portions 194-194g and seal portions 196-196g described above. The exemplary spring 266 may be of any suitable configuration that will permit the passage of fluid and, in the illustrated embodiment, includes a plurality of spaced radially extending arms that fit into a circumferentially extending slot 274 within the housing 254. The outlet valve 250 may be included in a wide variety of fluid transfer devices and/or implantable infusion devices such as, for example, those illustrated in U.S. Pat. No. 7,131,967.

Yet another exemplary valve is the regulator valve 276 in the pressure regulator 278 illustrated in FIG. 27. The regulator valve 276 includes an elastomeric valve seat 280, with a main portion 282 and a seal portion 284, and a valve element 286. The main portion 282 and seal portion 284 may be formed from the same materials, using the same manufacturing methods, as the valve seat main portions 194-194g and seal portions 196-196g described above. Although not limited to any particular configuration, the exemplary pressure regulator 276 also includes a housing 288 with an inlet 290, outlets 292, and a sealed bellows 294 that provides a reference pressure and carries the valve element 286. The pressure regulator 278 may be employed in an implantable infusion device (e.g. the implantable infusion device 200) upstream or downstream of the reservoir, either in direct or indirect fluidic communication with the pump, to prevent unintended discharge from the catheter as a result of over pressurization. Other exemplary pressure regulator configurations that may include a valve seat (or valve element) with the above-described main portion and seal portion configurations are disclosed in U.S. Pat. Pub. No. 2005/0273083.

Still another exemplary valve is the fill port valve 296 illustrated in FIG. 28, which opens and closes based on the volume of fluid within the associated reservoir to prevent an overfill. Although not limited to use in combination with any particular infusion device, the exemplary fill port valve 296 is shown in combination with the exemplary infusion device 200 and, to that end, the infusion device fill port 212 may include a chamfered inlet 213 and a septum 215. The exemplary fill port valve 296, which is in fluidic communication with the electromagnet pump 104 by virtue of its association with the reservoir 210, includes an outer housing portion 298 that is secured to the internal wall 206, an inner housing portion 300 with a valve seat 302 and valve seat lumens 304, a fixed cylinder 306 which functions as a needle stop and has a plurality of outlets 308 at various locations, a movable cylinder 310 which carries a valve element 312 with a main portion 314 and a seal portion 316. The seal portion 316 covers the entire surface of the main portion 314 that faces/engages the valve seat 302. The main portion 314 and seal portion 316 may be formed from the same materials, using the same manufacturing methods, as the valve seat main portions 194-194g and seal portions 196-196g described above. A spring or other biasing device 318, which is positioned at one end of the movable cylinder 310, biases the movable cylinder (and valve element 312) toward the valve seat 302. The other end of the movable cylinder 310 abuts the inner surface of the reservoir end wall 211. When the reservoir 210 is relatively empty, the force associated with the reservoir will overcome the force associated with the spring 318 and the movable cylinder 310 and valve element 312 will be in the position illustrated in FIG. 28.

The reservoir 210 may be filled by inserting a needle (not shown) into the fill port 212 and injecting fluid into the fixed cylinder 306. The fluid will flow into the reservoir 210 by way of the fixed cylinder outlets 308, the open end of the movable cylinder 310, and the valve seat lumens 304. The reservoir end wall 211 will move away from the wall 206 as the reservoir 210 fills with fluid. As this occurs, the biasing force of the spring 318 will drive the movable cylinder 310 away from the fill port 212. The reservoir 210 and fill port valve 296 are respectively configured such that, when the reservoir is full, the valve element 312 will engage the valve seat 302 and prevent additional flow through the valve seat lumens 304, thereby preventing an overfill condition.

Another exemplary fill port valve is generally represented by reference numeral 320 in FIG. 29. One example of an infusion device that may include the fill port valve 320 is the exemplary infusion device 200, which may have a fill port 212 with a chamfered inlet 213 and a septum 215. The fill port valve 320, which is in fluidic communication with the electromagnet pump 104 by virtue of its association with the reservoir 210, includes a housing 322 that is secured to the internal wall 206, a valve seat 324, and a valve element 326. The valve element 326, which has a main portion 328 and a seal portion 330, is carried by a valve element retainer 332 that is secured to the reservoir end wall 211 by a post 334. The main portion 328 and seal portion 330 may be formed from the same materials, using the same manufacturing methods, as the valve seat main portions 194-194g and seal portions 196-196g described above. When the reservoir 210 is relatively empty, the valve element 326 will be in the position illustrated in FIG. 29.

The reservoir 210 may be filled by inserting a needle (not shown) into the fill port 212 and injecting fluid into the housing 322. The fluid will flow into the reservoir 210 by way of an opening 336 in the valve seat 324 and the reservoir end wall 211 will move away from the wall 206 as the reservoir fills with fluid. The valve element 326 will move away from the fill port 212 by virtue of its connections to the reservoir end wall 211. The reservoir 210 and fill port valve 320 are respectively configured such that, when the reservoir is full, the valve element 326 will engage the valve seat 324 and prevent additional flow through the valve seat opening 336, thereby preventing an overfill condition.

Still another exemplary fill port valve is generally represented by reference numeral 338 in FIG. 30. One example of an infusion device that may include the fill port valve 338 is the exemplary infusion device 200, which may have a fill port 212 with a chamfered inlet 213 and a septum 215, The exemplary fill port valve 338 illustrated in FIG. 30, which is in fluidic communication with the electromagnet pump 104 by virtue of its association with the reservoir 210, is substantially similar to the valve illustrated in FIG. 29 and similar elements are represented by similar reference numerals. Here, however, the valve 338 includes a valve element 342 that is secured to the reservoir end wall 211. A valve seat 340, which has a main portion 344 and a seal portion 346, is secured to the housing 322. The main portion 344 and seal portion 346 may be formed from the same materials, using the same manufacturing methods, as the valve seat main portions 194-194g and seal portions 196-196g described above. When the reservoir 210 is relatively empty, the valve element head 348 will be in spaced relation to valve seat 340 so that fluid may flow though the valve seat opening 350.

The reservoir 210 may be filled by inserting a needle (not shown) into the fill port 212 and injecting fluid into the housing 322. The fluid will flow into the reservoir 210 by way of an opening 350 in the valve seat 340 and the reservoir end wall 211 will move away from the wall 206 as the reservoir fills with fluid. The valve element 342 will also move by virtue of its connection to the reservoir end wall 211. The reservoir 210 and fill port valve 338 are respectively configured such that, when the reservoir is full, the valve element head 348 will engage the valve seat 340 and prevent additional flow through the valve seat opening 350, as is shown in FIG. 30, thereby preventing an overfill condition.

Additional details concerning valves such as those illustrated in FIGS. 28-30, which open and close as a function of the volume of fluid within the reservoir, may be found in U.S. Pat. No. 5,158,547.

Another exemplary valve is the in-line pressure check valve 352 illustrated in FIG. 31, which uses a reference pressure to regulate flow. Although not limited to use in combination with any particular infusion device, the exemplary in-line pressure check valve 352 may be used in combination with the exemplary infusion device 200 and positioned between the reservoir 210 and fill port 212. The exemplary valve 352, which is in fluidic communication with the electromagnet pump 104 by virtue of its association with the reservoir 210, includes a base 354 with an annular chamber 356 and a central lumen 358, a control element 360 with lumens 362 and a valve element 364, and a flexible annular membrane 366 that seals the annular chamber 356 such that a reference pressure may be maintained within the chamber. The portion of the annular member 366 that is aligned with the valve element 364 is the valve seat 368. The valve seat 368 includes a main portion 370 and a seal portion 372 that may be formed from the same materials, using the same manufacturing methods, as the valve seat main portions 194-194g and seal portions 196-196g described above.

The exemplary in-line pressure check valve 352 is shown in its open state in FIG. 31. Fluid flowing from, for example, the fill port will pass though the control element lumens 362 and the base central lumen 358. Should the pressure of the fluid increase to a pressure that is greater than the reference pressure within the annular chamber 356, the flexible annular membrane 366 will deform into the annular chamber. The valve element 364 will then engage the valve seat 368, thereby preventing flow through the central lumen 358, when the fluid pressure reaches the rated pressure of the valve 352. Additional details concerning valves such as that illustrated in FIG. 31 may be found in U.S. Pat. No. 5,725,017.

The exemplary in-line pressure check valve 352 may also be modified in a variety of ways. For example, the pressure check valve 352a illustrated in FIG. 32 is substantially similar to the check valve 352 and similar elements are represented by similar reference numerals. Here, however, there is a separate valve seat 368a that is not part of the annular membrane 366. The valve seat 368a includes a main portion 370a and a seal portion 372a that may be formed from the same materials, using the same manufacturing methods, as the valve seat main portions 194-194g and seal portions 196-196g described above. Turning to FIG. 33, the in-line pressure check valve 352b illustrated in FIG. 32 is substantially similar to the check valve 352 and similar elements are represented by similar reference numerals. Here, however, the base 354b includes a valve seat 368b and the control element 360b carries a valve element 364b with main portion 370b and a seal portion 372b. The main portion 370b and seal portion 372b may be formed from the same materials, using the same manufacturing methods, as the valve seat main portions 194-194g and seal portions 196-196g described above.

Figure 34:
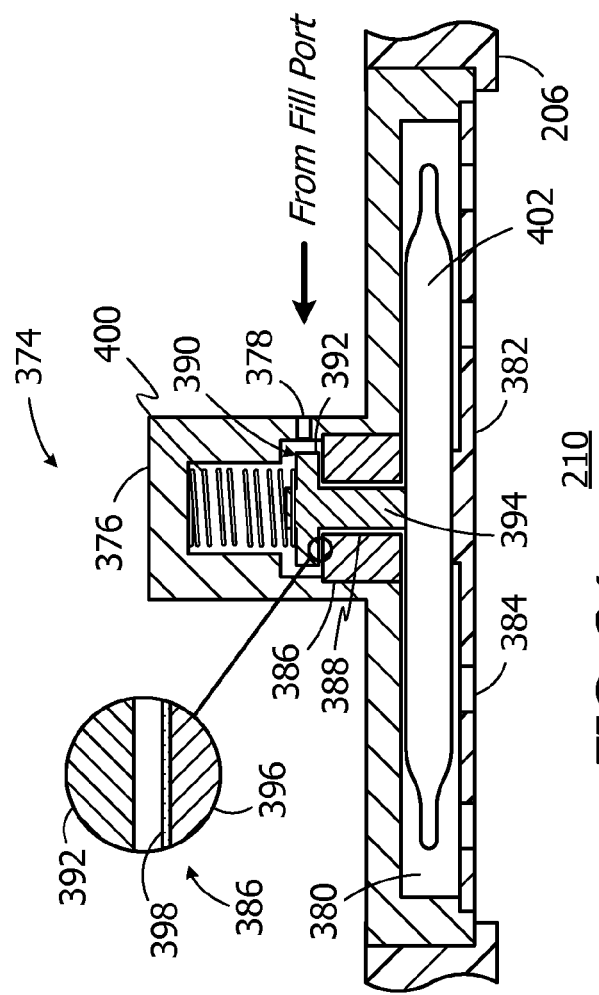
FIG. 34 is a partial section view of a pressure control valve in accordance with one embodiment of a present invention.

Another valve which uses a reference pressure to regulate flow is the exemplary pressure sensitive valve 374 illustrated in FIG. 34. One example of an infusion device that may include the valve 374 is the exemplary infusion device 200. The exemplary valve 374, which is in fluidic communication with the electromagnet pump 104 by virtue of its association with the reservoir 210, includes a housing 376 with an inlet port 378 that is in fluid communication with the fill port 212, and a recess 380 that is covered by a plate 382 with apertures 384. A valve seat 386 with a lumen 388 is secured to the housing 376 and a valve element 390, with a head 392 and a post 394, is positioned for movement relative to the valve seat. The valve seat 386 includes a main portion 396 and a seal portion 398 that may be formed from the same materials, using the same manufacturing methods, as the valve seat main portions 194-194g and seal portions 196-196g described above. The valve element 390 is biased toward the closed position, i.e. with the head 392 in contact with the valve seat 386, by a spring 400 or other suitable biasing element, and is biased toward the illustrated open position by collapsible sealed structure (or "aneroid") 402 that is secured to the post 394 and has an internal volume which is occupied by a fluid at a reference pressure.

The reference pressure within the sealed structure 402 will maintain the valve element 390 in the open position so that fluid may flow from the fill port to the reservoir 210 by way of the inlet port 378, lumen 388 and apertures 384. Should fluid flow continue after the reservoir 210 is full, the pressure on the exterior of the sealed structure 402 will increase to the point at which it will collapse. The collapse of the sealed structure 402 allows the spring 400 to drive the valve element 390 to its closed position where the head 392 is against the valve seat 386 and fluid is prevented from flowing through the lumen 388. Additional details concerning valves such that illustrated in FIG. 34 may be found in U.S. Pat. No. 6,152,898.

Figure 35:
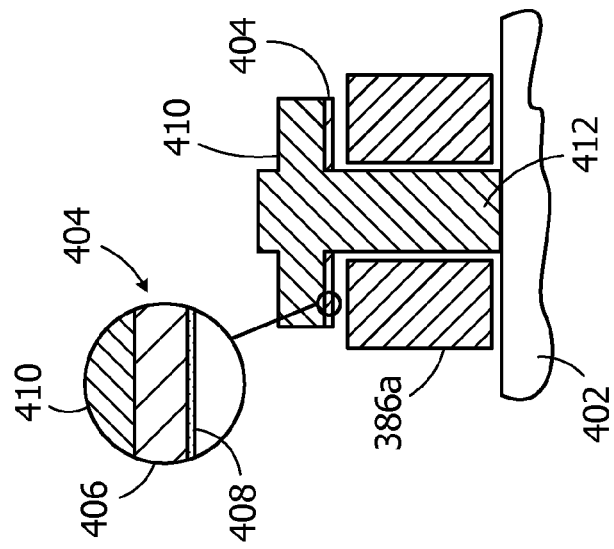
FIG. 35 is a section view of a portion of a pressure control valve in accordance with one embodiment of a present invention.

The exemplary pressure sensitive valve 374 may also be modified in a variety of ways. As illustrated for example in FIG. 35, a valve element 404, which has a main portion 406 and a seal portion 408, may be carried by a valve element retainer 410 that is secured to the sealed structure 402 by a post 412. The main portion 406 and seal portion 408 may be formed from the same materials, using the same manufacturing methods, as the valve seat main portions 194-194g and seal portions 196-196g described above. The valve element 404 will move in and out of contact with the valve seat 386a in response to pressure changes in the manner described above.

Turning to FIG. 36, the exemplary implantable infusion device 200a is substantially similar to the implantable infusion device 200 described above with reference to FIGS. 21-24 and similar elements are represented by similar reference numerals. Here, however, the implantable infusion device 200a includes catheter apparatus 414 with a header assembly 240a, a strain relief element 416 and a catheter 220. The header assembly 240a, which may be removably secured to the housing 202a in, for example, the manner described in U.S. Pat. No. 5,466,218, includes a check valve 418 between the catheter 220 and the side port 238. The check valve 418 is in fluid communication with the pump 104 when the header assembly 240a is secured to the housing 202a.

As illustrated in FIG. 37, the exemplary check valve 418 includes a housing 420 with an inlet 422 and an outlet 424, a valve seat 426, a valve element 428 and a spring 430 or other biasing device that biases the valve element to the closed position illustrated in FIG. 37. An o-ring 432 may be positioned between the valve element 428 and the spring 430. The housing may be an integral portion of the header assembly 240a (as shown) or may be a separate structural element. The exemplary valve element 428 is spherical and the valve seat 426 is configured to receive the spherical valve element. The valve seat 426 also includes a main portion 434 and a seal portion 436 that may be formed from the same materials, using the same manufacturing methods, as the valve seat main portions 194-194g and seal portions 196-196g described above. In other configurations, the valve element may be provided with a main portion and a seal portion formed from the same materials, using the same manufacturing methods, as the valve seat main portions 194-194g and seal portions 196-196g described above.

Another exemplary catheter assembly, which is generally represented by reference numeral 414a in FIG. 38, includes a catheter 220, a strain relief element 416a and a check valve 418a. The check valve 418a is essentially identical to the check valve 418 but for its location within the strain relief element 416a. The catheter assembly 414a may, in some instances, also include a removable header assembly such as that illustrated in FIG. 36.

Turning to FIG. 39, still another exemplary catheter assembly 414b includes a catheter 220 and a check valve 418b. The check valve 418b is essentially identical to the check valve 418 but for its size and its location within the catheter 220. The catheter assembly 414b may, in some instances, also include a strain relief element and/or a removable header assembly such as those illustrated in FIGS. 36 and 38.

The present inventions are also applicable to other types of ambulatory infusions devices and the valves employed therein. To that end, another example of an ambulatory infusion device in accordance with a present invention is the implantable infusion device generally represented by reference numeral 500 in FIGS. 40 and 41. The implantable infusion device 500 is similar to the implantable infusion device 200 in many respects and similar elements are represented by similar reference numerals. To that end, the exemplary infusion device 500 includes a housing 502 (e.g. a titanium housing) with a bottom portion 504, an internal wall 506, and a cover 508. An infusible substance (e.g. medication) may be stored in a reservoir 510 that is located within the housing bottom portion 504. The reservoir 510 may be replenished by way of a refill port 512 that extends from the reservoir, through the internal wall 506, to the cover 508. A hypodermic needle (not shown), which is configured to be pushed through the refill port 512, may be used to replenish the reservoir 510. The reservoir 510 in the exemplary infusion device 500 is a positive pressure reservoir and, in the illustrated embodiment, the reservoir is in the form of a titanium bellows that is positioned within a sealed volume defined by the housing bottom portion 504 and internal wall 506. The remainder of the sealed volume is occupied by a propellant P that exerts a positive pressure on the bellows.

The exemplary infusion device 500 also includes a fluid transfer device 100a that is configured for use in combination with a positive pressure reservoir such as the exemplary positive pressure reservoir 510. In the illustrated embodiment, the fluid transfer device 100a has an accumulator 544 that includes a housing 546, a diaphragm 548 (e.g. a flexible sheet of titanium), an inlet 550, and an outlet 552. The fluid transfer device 100a also has an active inlet valve 554, which controls the flow of fluid into the housing inlet 550, and an active outlet valve 556, which controls the flow of fluid out of the housing outlet 552. The active inlet valve 554 is also connected to the interior of the positive pressure reservoir 510, while the active outlet valve 556 is also connected to the outlet port 516 which, in turn, may be connected to the catheter 520. The exemplary active valves 554 and 556 are discussed in greater detail below with reference to FIGS. 42 and 43.

During operation of the fluid transfer device 100a, infusible substance will move from the positive pressure reservoir 510 to an accumulator cavity 558, which is defined by the housing 546 and the diaphragm 548, when the active inlet valve 554 is opened. A pressure chamber 562 is located on the other side of the diaphragm 548. The active outlet valve 556 will be closed while the inlet valve 554 is opened. The diaphragm 548 will flex due to the positive pressure from the reservoir until it reaches a stop 560, as is shown in dashed lines in FIG. 41, thereby increasing the volume of the accumulator cavity 558 by a predetermined amount. The active inlet valve 554 will then be allowed to close. When the active outlet valve 556 is opened, the pressure within the chamber 562 will drive the diaphragm 548 back to the solid line position, thereby driving the predetermined volume of fluid to the outlet port 516.

Figure 42:
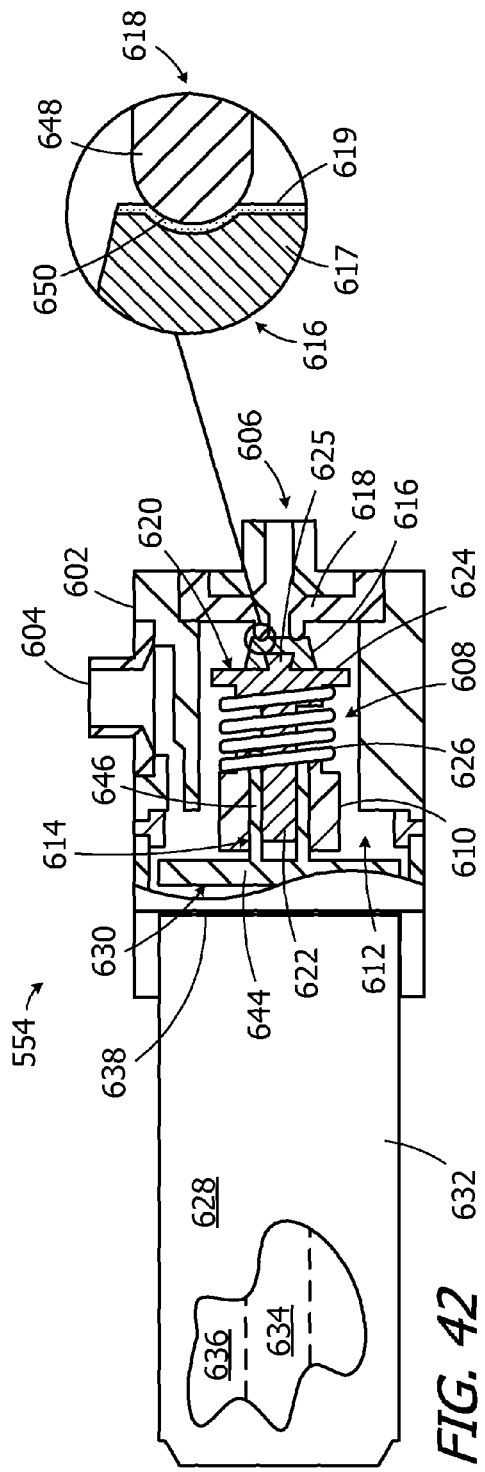
FIG. 42 is a partial section view of a valve in accordance with one embodiment of a present invention.
Figure 43:
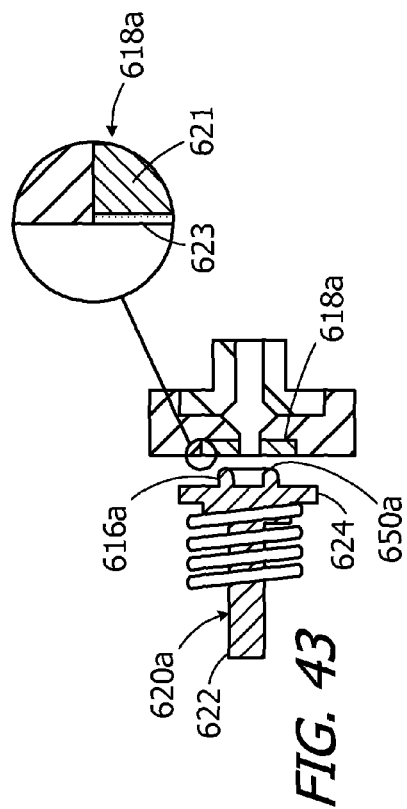
FIG. 43 is a partial section view of a portion of a valve in accordance with one embodiment of a present invention.

Although the present fluid transfer device 100a is not so limited, the active inlet and outlet valves 554 and 556 in the illustrated embodiment are identical electromagnet valves that may be selectively actuated in a manner similar to the electromagnet pumps described above. Turning to FIG. 42, the exemplary active inlet valve 554 (and outlet valve 556) includes a generally solid, cylindrical housing 602 with various open regions that accommodate portions of various structures and define a fluid flow path. More specifically, the housing 602 includes an inlet 604, an outlet 606 and an open region 608. The inlet 604 may be used as an outlet, and the outlet 606 may be used as an inlet, when the direction of fluid flow through the valve 554 is reversed. A spring retainer 610, with apertures 612 to permit fluid flow and a bore 614, is mounted within the housing 602.

An elastomeric valve element 616 is movable in to and out of engagement with a rigid valve seat 618 that is associated with the outlet 606. The valve element 616 includes a main portion 617 and a seal portion 619. The valve element main portion 617 and seal portion 619 may be formed from the same materials, using the same manufacturing methods, as the valve seat main portions 194-194g and seal portions 196-196g described above. The elastomeric valve element 616 is supported on a valve element retainer 620 that includes a shaft 622, a spring retainer 624 and an anchor 625. A spring 626 (e.g. a coil spring), which is mounted between the spring retainers 610 and 624, biases the valve element retainer 620 to the closed position illustrated in FIG. 42 such that the valve element 616 engages the valve seat 618.

With respect to actuation, the exemplary active valve 554 also includes an electromagnet 628 and an armature 630. The electromagnet 628, which is carried within a case 632 that is secured to the housing 602, has a core 634 and a coil 636. The case 632 and core 634 are made from a magnetic material. The coil 636 consists of a wire or other conductor that is wound around the core 634. The coil 636 may be insulated from the case 632 by electrically non-conductive spacers (not shown), which center the coil within the case, or through the use of potting compound or encapsulant material between the case and the coil. A barrier 638 separates the open region 608, which will ultimately be filled with fluid, from the electromagnet 628. The armature 630 consists of a pole 644 formed from a magnetic material (e.g. magnetic steel), which is located within the open region 608 such that it will be magnetically attracted to the electromagnet 628 when the electromagnet is actuated, and a hollow cylindrically-shaped bushing 646 that extends from the pole and into the bore 614 and is slidable relative to the bore. The valve element retainer shaft 622 is fixedly secured (e.g. through a press fit) to the armature pole 644 by way of the bushing 646. The magnetic attraction between the actuated electromagnet 628 and the armature pole 644 is sufficient to overcome the biasing force of the spring 626 and move the valve element 616 away from the valve seat 618 to open the active valve 554.

The exemplary valve seat 618 illustrated in FIG. 42, which is rigid and has an overall circular shape, includes a main portion 648 and a curved surface 650 that is semi-circular or otherwise curved in cross-section. The curved surface 650 reduces the contact area between the valve seat 618 and the valve element 616, which in turn increases the sealing pressure, as compared to a sealing arrangement that has two flat surfaces. The curved surface 650 also eliminates the adhesion force associated with flat on flat contact surfaces. The scuffing issue discussed above is also obviated because the rigid valve seat 618 does not have sharp edges that come into contact with the elastomeric valve element 616.

In other implementations, a substantially rigid valve element 616a (FIG. 43) may be provided with a curved surface 650a that is semi-circular or otherwise curved in cross-section and is carried by a valve element carrier 620a. The curved surface 650a engages an elastomeric valve seat 618a when the valve is closed. This arrangement is analogous to, and provides the same benefits as, the curved seal arrangement illustrated in FIG. 42. The valve seat 616a includes a main portion 621 and a seal portion 623. The valve seat main portion 621 and seal portion 623 may be formed from the same materials, using the same manufacturing methods, as the valve seat main portions 194-194g and seal portions 196-196g described above.

With respect to manufacturing and materials, the exemplary housing 602 is a machined part and suitable materials for the housing include, but are not limited to, titanium, titanium alloys, stainless steel (e.g. 316L stainless steel), cobalt-nickel alloys, and refractory metals such as tantalum. The valve element retainer 620 may also be machined and suitable materials for the machined valve element include, but are not limited to, those described above in the context of the housing 602. Alternatively, the valve element retainer 620 may be molded. Suitable materials for a molded valve element include, but are not limited to, polyolefins, liquid crystal polymers, PEEK, polyacetal plastics such as Delrin®, fluoropolymers, and most other molded materials that are rigid and inert to pharmaceuticals.

Additional information concerning the exemplary fluid transfer device 100a and/or active valves may be found in U.S. Pat. Nos. 4,838,887 and 5,368,274, which are incorporated herein by reference. It should also be noted here that, although the active valves in the illustrated embodiments include electromagnet actuators, other types of actuators may also be employed. For example, solenoid and piezoelectric actuators may be employed.

Energy for the active valves 554 and 556, as well for other aspects of the exemplary infusion device 500, is provided by the implantable infusion device battery (not shown). The battery charges one or more capacitors in the manner described above, and is not directly connected to the active valves themselves. The capacitor(s) are selectively connected to one of the electromagnet coils 636 in the active valves 554 and 556, and disconnected from the battery, when an electromagnet coil is being energized, and are disconnected from the electromagnet coils and connected to the battery when the capacitor(s) are being recharged and/or when the fluid transfer device 100a is at rest.

As discussed above in the context of infusion device 200, the capacitor(s) are carried on a board along with an RF communication device that is connected to an antenna. The communication device may, alternatively, be an oscillating magnetic field communication device, a static magnetic field communication device, an optical communication device, an ultrasound communication device, a direct electrical communication device, or other suitable device. A controller 534 (FIG. 41), such as a microprocessor, microcontroller or other control circuitry, is carried on the other side of the board. The controller controls the operations of the infusion device 500 in accordance with instructions stored in memory and/or provided by and external device by way of the aforementioned communication device. For example, the controller 534 may be used to control the fluid transfer device 100*a* to supply fluid to the patient in accordance with, for example, a stored basal delivery schedule or a bolus delivery request, by selectively actuating (i.e. opening) and de-actuating (i.e. closing) the active valves 554 and 556.

Figure 41:
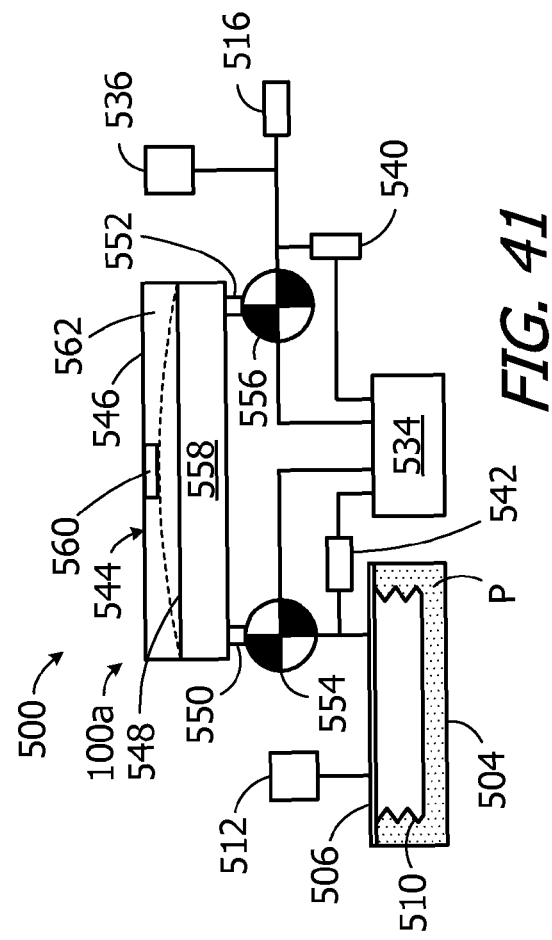
FIG. 41 is a schematic view of the implantable infusion device illustrated in FIG. 40.
Figure 40:
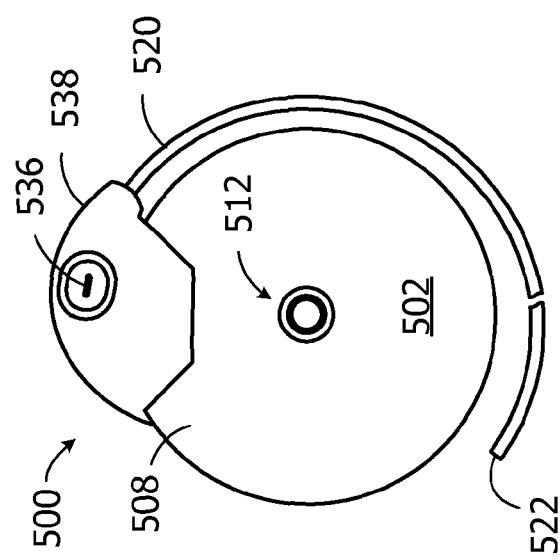
FIG. 40 is a plan view of an implantable infusion device in accordance with one embodiment of a present invention.

Referring to FIGS. 40 and 41, the exemplary infusion device 500 is also provided with a side port 536 that is connected to a passageway between the outlet of the active valve 556 and the outlet port 516. The side port 536 facilitates access to an implanted catheter 520, typically by way of a hypodermic needle. For example, the side port 536 allows clinicians to push fluid into the catheter 520 and/or draw fluid from the catheter. The outlet port 516, a portion of the associated passageway, the antenna and the side port 536 are carried by a header assembly 538. The header assembly 538 is a molded, plastic structure that is secured to the housing 502. The housing 502 also includes a small aperture through which portions of the passageway are connected to one another, and a small aperture through which the antenna is connected to the board.

The exemplary infusion device 500 may include a pressure sensor 540 between the active valve 556 and the outlet port 516. As such, the pressure sensor 540 senses the pressure at the outlet port 516 which, in the illustrated embodiment, is also the pressure within the catheter 520. Another pressure sensor 542 may also be between the reservoir 510 and the active valve 554. The pressure sensor 542 may be used to measure the reservoir pressure. The pressure sensors 540 and 542, which are connected to the controller 534, may also be used to measure the pressure differential across the fluid transfer device 100*a* and to analyze a variety of aspects of the operation of the exemplary infusion device 500. For example, pressure measurements may be used to determine whether or not there is a complete or partial blockage in the catheter 520.

Although the inventions disclosed herein have been described in terms of the preferred embodiments above, numerous modifications and/or additions to the above-described preferred embodiments would be readily apparent to one skilled in the art. By way of example, but not limitation, the present inventions have application in infusion devices that include multiple reservoirs and/or outlets. Moreover, the inventions include any and all combinations of the elements from the various embodiments disclosed in the specification. It is intended that the scope of the present inventions extend to all such modifications and/or additions and that the scope of the present inventions is limited solely by the claims set forth below.

We claim:

1. A valve, comprising:
a valve housing including an opening;
a valve seat that extends around the opening;
a valve element that is movable relative to the valve seat between a closed position where the valve element engages the valve seat to prevent flow through the opening and an open position where the valve element is in spaced relation to the valve seat to allow flow through the opening; and a spring that biases the valve element against the valve seat;
wherein one of the valve seat and the valve element includes a main portion and a seal portion that is less tacky than the main portion and is in contact with the other of the valve seat and the valve element when the valve element is in the closed position.

2. The valve claimed in claim 1, wherein
the housing includes a circumferentially extending slot; and
a portion of the spring is located within the slot.

3. The valve claimed in claim 1, wherein
the spring is configured to permit the passage of fluid therethrough.

4. The valve claimed in claim 1, further comprising:
the valve element includes a carrier that mounts the valve element on the spring.

5. The valve claimed in claim 1, wherein
the valve element includes the main portion and the seal portion that is less tacky than the main portion.

6. The valve claimed in claim 1, wherein the valve element includes an uneven surface that engages the valve seat.

7. The valve claimed in claim 1, wherein
the valve element has an end portion that faces the opening;
the end portion faces the opening and is aligned with the opening when the valve element is in the open position; and
the end portion faces the opening and is aligned with the opening when the valve element is in the closed position.

8. The valve claimed in claim 1, wherein
the valve element faces the opening and is aligned with the opening when the valve element is in the open position; and
the valve element faces the opening and is aligned with the opening when the valve element is in the closed position.

9. The valve claimed in claim 1, wherein
the main portion and the seal portion are formed from different materials.

10. A valve, comprising:
a valve housing including an opening;
a valve seat that extends around the opening; and
a valve element that is movable relative to the valve seat between a closed position where the valve element engages the valve seat to prevent flow through the opening and an open position where the valve element is in spaced relation to the valve seat to allow flow through the opening;
wherein one of the valve seat and the valve element includes a main portion, formed from an elastomeric material selected from the group consisting of silicone rubber, latex rubber, fluoropolymers, urethane, butyl rubber, and isoprene, and a seal portion that is less tacky than the main portion and is in contact with the other of the valve seat and the valve element when the valve element is in the closed position.

11. The valve claimed in claim 10, wherein
the valve element includes the main portion and the seal portion that is less tacky than the main portion.

12. The valve claimed in claim 10, wherein the valve element includes an uneven surface that engages the valve seat.

13. A valve, comprising:
a valve housing including an opening;

a valve seat that extends around the opening; and a valve element that is movable relative to the valve seat between a closed position where the valve element engages the valve seat to prevent flow through the opening and an open position where the valve element is in spaced relation to the valve seat to allow flow through the opening;

wherein one of the valve seat and the valve element includes a main portion and a seal portion that is less tacky than the main portion and is in contact with the other of the valve seat and the valve element when the valve element is in the closed position;

the main portion is formed from an elastomeric material; and the seal portion is selected from the group consisting of
- a layer of silicon suboxide on the main portion,
- a relatively thin layer of a relatively hard elastomeric material,
- a relatively thin layer of a fluoroelastomer or a low friction protective coating, and
- a coating of a filler material.

14. The valve claimed in claim 13, wherein the valve element includes the main portion and the seal portion that is less tacky than the main portion.

15. The valve claimed in claim 13, wherein the valve element includes an uneven surface that engages the valve seat.

16. A valve, comprising:

a valve housing including an opening;

a valve seat that extends around the opening; and a valve element that is movable relative to the valve seat between a closed position where the valve element engages the valve seat to prevent flow through the opening and an open position where the valve element is in spaced relation to the valve seat to allow flow through the opening;

wherein one of the valve seat and the valve element includes a main portion and a seal portion that is less tacky than the main portion and is in contact with the other of the valve seat and the valve element when the valve element is in the closed position;

the main portion is formed from an elastomeric material; and the seal portion is selected from the group consisting of
- a surface of the valve seat main portion that has been halogenated,
- a surface of the valve seat main portion that has been implanted with ions of a ceramic material or ions of a metal material or ions of a metal oxide material, and
- a surface of the valve seat main portion that has been implanted and coated with ions of a ceramic material or ions of a metal material or ions of a metal oxide material.

17. The valve claimed in claim 16, wherein the valve element includes the main portion and the seal portion that is less tacky than the main portion.

18. The valve claimed in claim 16, wherein the valve element includes an uneven surface that engages the valve seat.

* * * * *